United States Patent [19]
Katz et al.

[11] Patent Number: 5,534,554
[45] Date of Patent: Jul. 9, 1996

[54] SUCROSE ESTER-C20 TO C28 ALCOHOL FORMULATIONS

[75] Inventors: David H. Katz, La Jolla; Mohammed H. Khalil; John F. Marcelletti, both of San Diego; Laura E. Pope, Carlsbad; Lee R. Katz, La Jolla, all of Calif.

[73] Assignee: Lidak Pharmaceuticals, La Jolla, Calif.

[21] Appl. No.: 299,944

[22] Filed: Sep. 2, 1994

Related U.S. Application Data

[63] Continuation-in-part of Ser. No. 166,523, Dec. 13, 1993, abandoned.

[51] Int. Cl.⁶ .................. A61K 31/045; A61K 9/107; A61K 9/06; A61K 7/48
[52] U.S. Cl. .................. 514/724; 514/789; 514/873; 514/939; 514/975
[58] Field of Search .................. 514/724, 789, 514/873, 939, 975

[56] References Cited

U.S. PATENT DOCUMENTS

| | | |
|---|---|---|
| 4,186,211 | 1/1980 | Debat . |
| 4,200,655 | 3/1980 | Farah et al. . |
| 4,536,519 | 8/1985 | Svzuki et al. . |
| 4,624,966 | 11/1986 | Yamamoto et al. . |
| 4,670,471 | 6/1987 | Clark . |
| 4,684,479 | 8/1987 | D'Arrigo . |
| 4,865,848 | 9/1989 | Cheng et al. . |
| 4,874,794 | 10/1989 | Katz . |
| 4,900,555 | 2/1990 | Cheng et al. . |
| 4,940,586 | 7/1990 | Cheng et al. . |
| 4,956,171 | 9/1990 | Chang . |
| 5,070,107 | 12/1991 | Katz . |
| 5,154,855 | 10/1992 | Sekiguchi et al. . |
| 5,166,219 | 11/1992 | Katz . |
| 5,194,451 | 3/1993 | Katz, II . |

FOREIGN PATENT DOCUMENTS 0158108  10/1985  European Pat. Off. .

OTHER PUBLICATIONS

McBride et al. (1987) Evaluation of Triacontanol–Containing Compounds as Anti–Inflammatory Agents Using Guinea Pig Models. J. Invest. Dermatol. 89:380–83.

Snipes et al. (1977) Inactivation of Lipid–Containing Viruses by Long–Chain Alcohols. Antimicrob. Agents & Chemother. 11:98–104.

Sands et al. (1979) Extreme Sensitivity of Enveloped Viruses, including Herpes Simplex, to Long–Chain unsaturated Monoglycerides and Alcohols. Antimicrob. Agents Chemother. 15:67–73.

*Primary Examiner*—Shep K. Rose
*Attorney, Agent, or Firm*—Knobbe, Martens, Olson & Bear

[57] ABSTRACT

A stable, efficacious therapeutic cream wherein a principal therapeutic compounds are one or more C-20 to C-28 long chain aliphatic alcohols, of which n-docosanol is exemplary, comprising sucrose cocoate, sucrose stearates or sucrose distearate, or mixtures thereof, is disclosed.

22 Claims, 9 Drawing Sheets

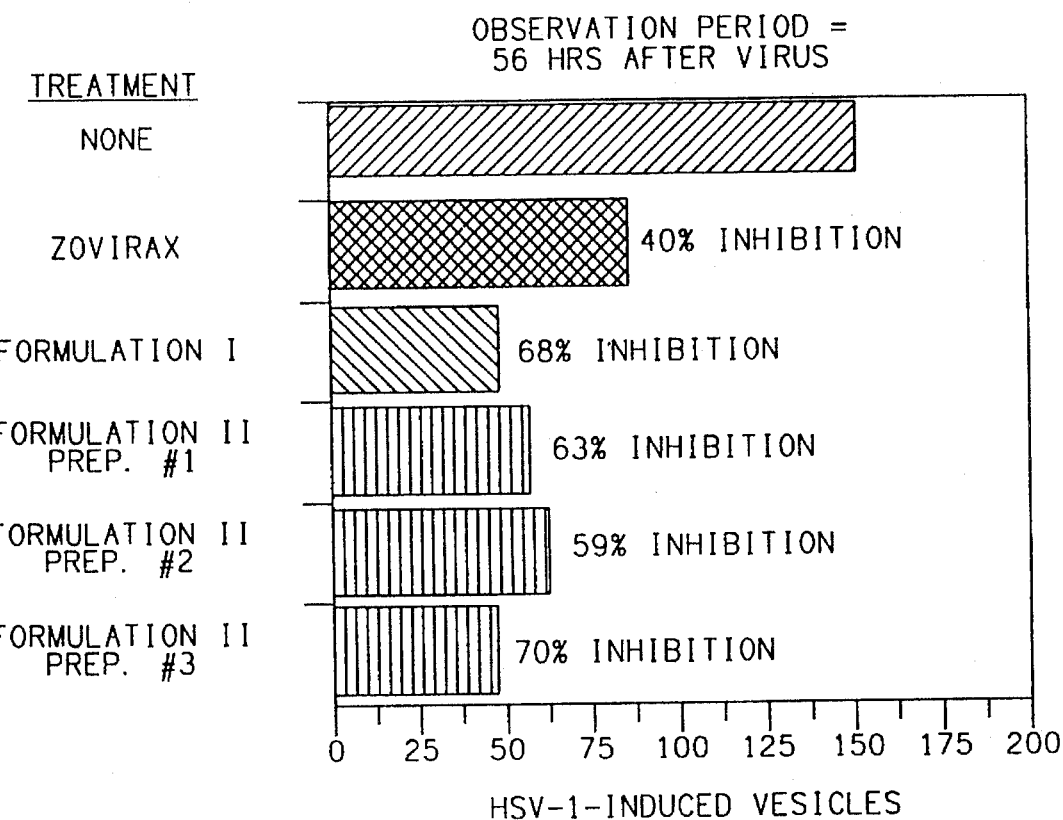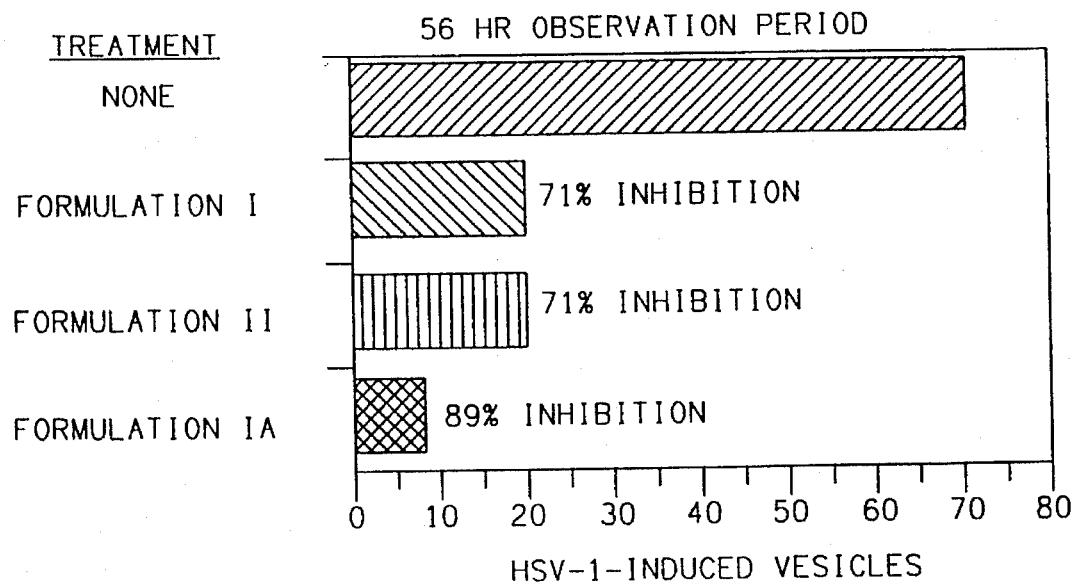

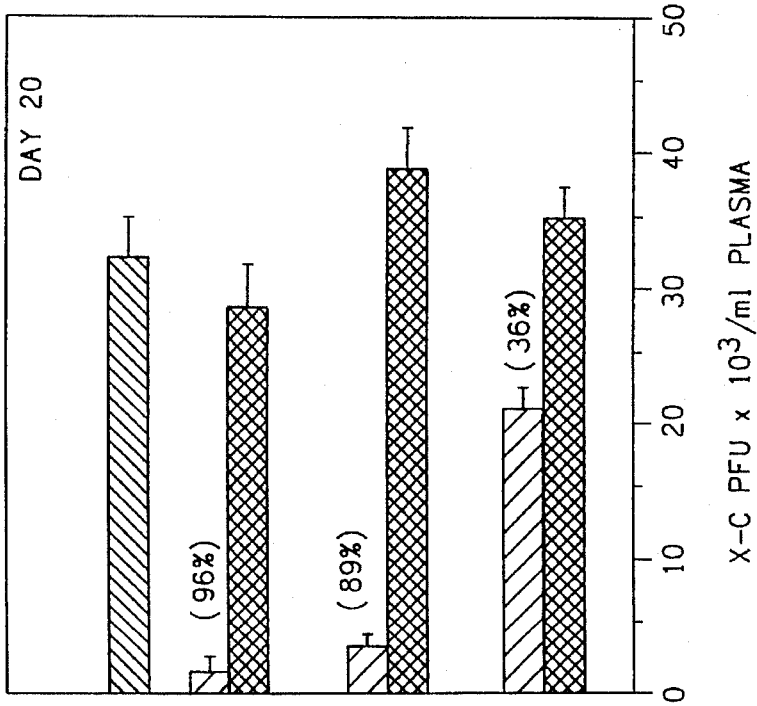
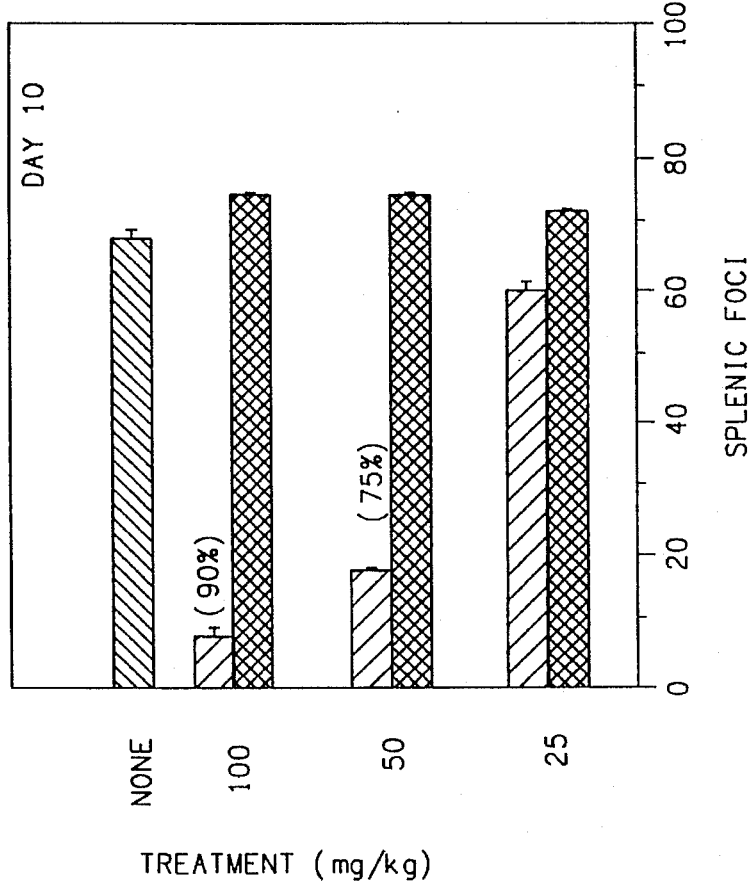
FIG. 12

SUCROSE ESTER-C20 TO C28 ALCOHOL FORMULATIONS

CROSS-REFERENCE TO RELATED APPLICATION

This is a continuation-in-part of U.S. patent application Ser. No. 08/166,523, Filed Dec. 13, 1993 now abandoned, to which priority is claimed.

FIELD OF THE INVENTION

This invention relates to topical therapeutic preparations and methods for treating viral and inflammatory diseases and for reducing the pain of topical intimation of skin and mucous membranes. Exemplary of the preparations of this inventions are creams containing 20 to 28 carbon aliphatic alcohols, of which n-docosanol is exemplary.

BACKGROUND OF THE INVENTION

Most antiviral therapeutic compounds block various specific viral genetic replicative mechanisms within infected target cells. These approaches have drawbacks including toxicity to host cells, induction of drug-resistant viral substrains, and the potential to act as mutagens and/or teratogens for host cells. Consequently, the search for new antiviral compounds that will provide efficacious therapy, without such deleterious consequences to the host, is of paramount importance. This is particularly true as we appear to enter a new age of vulnerability to heretofore obscure viruses of the retroviral family.

Compounds that exert antiviral activities without being potentially detrimental to the infected host have been identified and have shown some promising results. In the late 1970's, for example, Snipes and colleagues (W. Snipes, S. Person, G. Keller, W. Taylor, A. Keith, Antimicrob. Agents Chemother. 11, 98–104 (1977); J. Sands, D. Auperin, W. Snipes, Antimicrob. Agents Chemother. 15, 67–73 (1979)) reported a series of studies demonstrating such activities for both saturated and unsaturated alcohols of moderate chain lengths. Optimal antiviral activity was observed with 10–12 carbon-long saturated alcohols; less antiviral activity was observed with alcohols 14–18 carbons long, and alcohols of higher chain lengths were not tested. While significant antiviral activity was observed with C-10 and C-12 alcohols, these compounds also exhibited cytotoxic and hemolytic effects. Similar observations were made with unsaturated alcohols and monoglycerides, peak activity occurring with C-18 alcohol containing three double bonds. Subsequently, Clark and colleagues (L. L. Clark, Treatment for inflammatory skin disease. U.S. Pat. No. 4,670,471 (1987); P. T. McBride, L. L. Clark, G. G. Krueger, J. Invest. Dermatol. 89, 380–383 (1987)) concluded that the 30 carbon-long saturated alcohol, triacontanol, was active as an anti-herpes agent. However, since tissue culture studies demonstrated that triacontanol lacked direct antiviral activity, it was speculated that the apparent anti-herpes activity observed in animal studies might reflect a putative immunomodulatory effect of this compound.

As early as 1974, n-docosanol was reported to have systemic therapeutic value. For example, Debar, U.S. Pat. No. 4,186,211, reported that 1-docosanol when taken orally was therapeutically effective in the treatment of enlargement of the prostate gland. Similar work was reported a decade later by Yamamoto, et. al, e.g. U.S. Pat. No. 4,624,966, who, incorrectly as to chemical nomenclature, listed n-docosanol as a polyprenyl compound and described the peroral or parenteral administration of n-docosanol in therapy. Neither Debat nor Yamamoto, et. al, nor any other workers, have, to the knowledge of the present inventors, suggested even remotely, the possibility that n-docosanol might be an active agent in topical therapy.

After examining the results of Snipes and colleagues, and realizing that compounds longer than 18 carbons had not been examined to ascertain if they might exhibit topical antiviral or inflammatory activity, we reasoned that a molecule twice as long as C-10 or C-12 (which had displayed peak antiviral, but also cytotoxic and hemolytic activity) might retain biological activity against viruses, but (perhaps because of folding-over of the molecule) lack the hemolytic and cytotoxic property of the shorter molecule. Studies in our laboratory testing the antiviral properties of n-docosanol were favorable (Katz, D. H., U.S. Pat. No. 4,874,794).

The preparation of stable, efficacious n-docosanol-containing topical formulations, however, presented a challenge. While creams and ointments of certain conventional formulation were initially adequate for preliminary evaluations, we found that certain excipients were detrimental to the activity of n-docosanol. It became obvious, therefore, that there was a need for reproducibly effective formulations of n-docosanol that were stable for long periods of time, physiologically acceptable and suitable for topical application to skin and membranes. The preparation of stable, effective n-docosanol-containing compositions presented an unexpectedly difficult challenge. Conventional cream formulations that are entirely suitable for preparing carrier creams for most pharmaceuticals were not satisfactory. While penetration enhancing compounds were considered as possibly desirable, increasing penetration enhancement was not a particular problem. Many penetration enhancers are available but there was no reason to consider such materials vis-a-vis penetration enhancement and certainly no reason to expect that any of these materials would result in a cream that would result in enhanced pharmaceutical efficacy and would be stable at all temperatures such a product would encounter during storage and handling, and for all time periods that would expected in normal storage and handling and, in addition, be stable through phase changes and/or being exposed to temperatures well below the freezing point of the aqueous constituent of the cream and in which the highly hydrophobic long chain alcohols of this invention would retain pharmacological activity. Azone, reported by Rajadhyaksha, for example, is an excellent penetration enhancer but has not been known as a stabilizing constituent in cream formulations. Sucrose esters of coconut fatty acids have been formulated as penetration enhancers, Cheng. et. al., U.S. Pat. No. 4,865,848, and other patents. Cheng, et. al., do not suggest, however, any cream stabilization resulting from these materials, nor is there any reason to infer such stabilization from the Cheng, et. al. patents. Literature on such compounds does not suggest these materials as being particularly effective in stabilizing C-20 to C-28 aliphatic alcohol-containing creams. It is to the solution of these problems that this invention is directed. Specifically, this invention is directed to an efficacious, stable, physiologically acceptable cream suitable for topical application of C-20 to C-28 aliphatic alcohols, e.g. n-docosanol, for therapy.

A variety of formulae compositions were experimentally tested as to stability and providing a cream in which the long chain alcohols exhibited high physiological activity in a topical cream. Some formulations exhibit poor stability and some exhibited poor physiological activity. Only the formulations that are the subject of this invention were found to be satisfactory as to stability and activity.

One significant result came as a complete surprise—the immediate reduction and sometimes complete relief from the pain of inflammation of the skin and mucous membranes.

SUMMARY OF THE INVENTION

This invention is embodied in a therapeutic cream in which the principal physiologically active therapeutic composition is a long chain aliphatic alcohol having from 20 to 28 carbon atoms, i.e., n-icosanol, n-henicosanol, n-docosanol, n-tricosanol, n-tetracosanol, n-pentacosanol, n-hexacosanol, n-heptacosanol, and n-octacosanol, or mixtures thereof, for the relief of the pain of dermal and membranal inflammation. n-Docosanol is the most readily available of this family of straight chain saturated alcohols and is the exemplary compound in many experiments.

This invention is also embodied in the manufacture of therapeutic creams using sucrose and equivalent sugar-based esters that have been found to have a unique ability to stabilize creams containing at least one long chain aliphatic alcohol having from 20 to 28 carbon atoms, i.e., n-icosanol, n-henicosanol, n-docosanol, n-tricosanol, n-tetracosanol, n-pentacosanol, n-hexacosanol, n-heptacosanol, and n-octacosanol, or mixtures thereof, n-docosanol alone or in mixture with other such alcohols being exemplary.

The present invention is embodied in a topical cream formulation suitable for use in treating virus-induced and inflammatory diseases of the skin or membranes of an animal, including the treatment of humans. The essential ingredients of the cream are at least one long chain aliphatic alcohol having from 20 to 28 carbon atoms, i.e., n-icosanol, n-henicosanol, n-docosanol, n-tricosanol, n-tetracosanol, n-pentacosanol, n-hexacosanol, n-heptacosanol, and n-octacosanol, or mixtures thereof, n-docosanol alone or in mixture with other such alcohols being exemplary, the physiologically active ingredient, water, oil, an ester of a sugar and a fatty acid, the ester being physiologically inert or capable of being metabolized by the body, and an emollient to assist in penetration of the n-docosanol into the affected area of the skin or membrane. As indicated equivalent but much less available and much more expensive aliphatic alcohols than n-docosanol, having a chain length of from about 20 to 28 may be used along with or in lieu of the n-docosanol. The sugar-based esters comprise a sugar moiety having a molecular weight of greater than about 150 and preferably above 250 and a fatty acid ester moiety having a molecular weight of about 150 or higher, and preferably above 250; the ester having a molecular weight of about 400 or higher. Sugars, as the term is used here, are sweet or sweetish carbohydrates that are ketonic or aldehydic derivatives of higher polyalcohols, and include both saccharides and disaccharides, disaccharide-based esters being preferred. High molecular weight polyhydric alcohols may be substituted with satisfactory but less than optimum results and, to that extent, are equivalent to more traditional sugars. Examples of such esterified sugar-based surfactants can be found in the chemical literature generally and in various catalogs, e.g. McCutcheon's directories, Volume 1—EMULSIFIERS & DETERGENTS, and Volume 2—FUNCTIONAL MATERIALS, (McCutcheon's Division, The Manufacturing Confectioner Publishing Co., Glen Rock, N.J., USA, 1993). Sucrose-fatty acid esters are preferred and are used in the examples given hereinafter.

A generally optimum cream formulation comprises, by weight percent:

| | |
|---|---|
| n-Docosanol* | 5–25% or more, though higher amounts would not be more beneficial than lower amounts, optimally about 10% ± 5%; |
| sucrose stearates | 0–15%, optimally about 3 to 10% (by weight); |
| sucrose cocoate | 0–15%, optimally about 3 to 10%; |
| sucrose distearate | 0–15%, optimally about 3 to 10%; with the proviso that at least one sucrose ester or an equivalent sugar-based ester is present and that sugar-based ester(s) comprise about 3 weight percent or more, preferably about 10 ± 5 weight percent of the total composition; |
| nuneral oil NF | 3–15%, optimally about 8% ± 4%; |
| propylene glycol USP | 2–10%, or functionally equivalent emollient, optimally about 5% ± 2%; |
| polyoxypropylene-15-stearyl ether | 0–5%, optimally about 2–3%; |
| benzyl alcohol NF | 0–5%, optimally about 2–3%, with the proviso that either polyoxypropylene-15-stearyl ether or benzyl alcohol or a functional equivalent thereof, be present in an amount of at least 1%; and |
| water | 40–70%, optimally about 45 to 65%. |

*Or at least one long chain aliphatic alcohol having from 20 to 28 carbon atoms, i.e., n-icosanol, n-henicosanol, n-docosanol, n-tricosanol, n-tetracosanol, n-pentacosanol, n-hexacosanol, n-heptacosanol, and n-octacosanol, or mixtures thereof, n-docosanol alone or mixed with such alcohols being exemplary.

The invention is embodied in methods of treating topical virus infections using the creams of the invention.

In a more general sense, the invention is embodied in the topical treatment of inflamed tissues generally.

BRIEF DESCRIPTION OF THE DRAWINGS

FIGS. 1 through 3 and FIGS. 6A, 6B are experiments involving herpes simplex virus type 1 (HSV-1), while FIGS. 4 and 5 and FIGS. 7 through 9 involve herpes simplex virus type 2 (HSV-2).

FIG. 1 presents the comparative activities of Formulation I (n-docosanol 10.0%; sucrose stearates 11.0%; sucrose cocoate 5.0%; mineral oil 8.0%; propylene glycol 5.0%; 2-ethyl-1,3-hexanediol 2.7% and purified water 58.3%), three different preparations of Formulation II (same as Formulation I except 5% sucrose stearates was replaced with sucrose distearate and ethyl hexanediol was replaced with an equivalent amount of polyoxypropylene-15-stearyl ether)

Figure 3A:
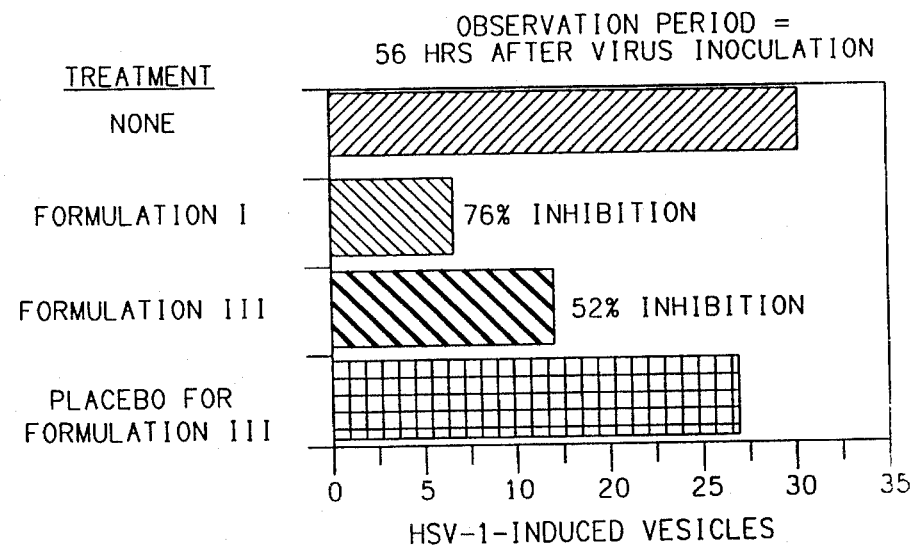

and ZOVIRAX( (acyclovir; Burroughs Wellcome Co., Research Triangle Park, N.C.; the current agent of choice for treatment of HSV infections which inhibits activity of viral DNA polymerase) in inhibiting HSV-1-induced cutaneous lesions in hairless guinea pigs.

FIG. 2 presents the comparative activities of Formulation I, Formulation II and Formulation IA (n-docosanol 10.0%; sucrose stearates 11.0%; sucrose cocoate 5.0%; mineral oil 8.0%; propylene glycol 5.0%; benzyl alcohol 2.7% and purified water 58.3%).

FIG. 3A shows a comparison of activities of Formulation I versus Formulation III (n-docosanol 10.0%; sucrose stearates 5.0%; mineral oil 8.0%; propylene glycol 5.0%; benzyl alcohol 2.7%; and purified water 58.3%).

Figure 3B:
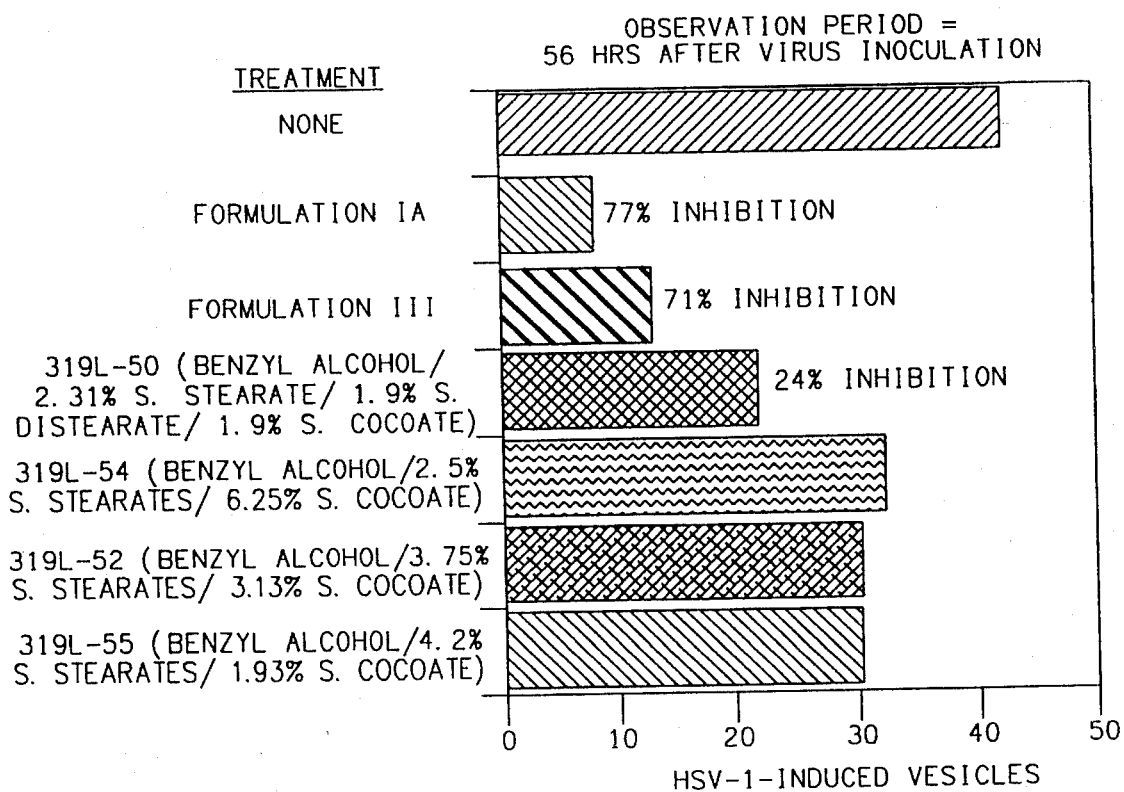

FIG. 3B depicts data comparing the activities of certain modifications of these formulations in which the relative surfactant concentrations have been modified from that of Formulation I. Modifications of surfactant concentrations were found to have appreciable deleterious effects on the extent of drug activity.

Figure 4:
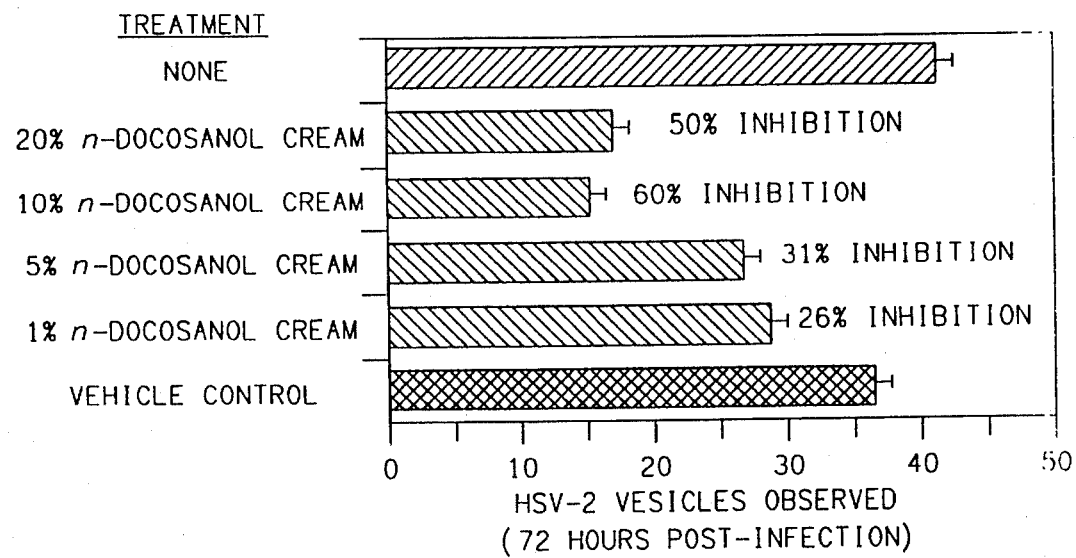

FIG. 4 depicts data showing the dose-response relationship of Formulation III for the inhibition of HSV-2 induced cutaneous lesions in hairless guinea pigs.

Figure 5:
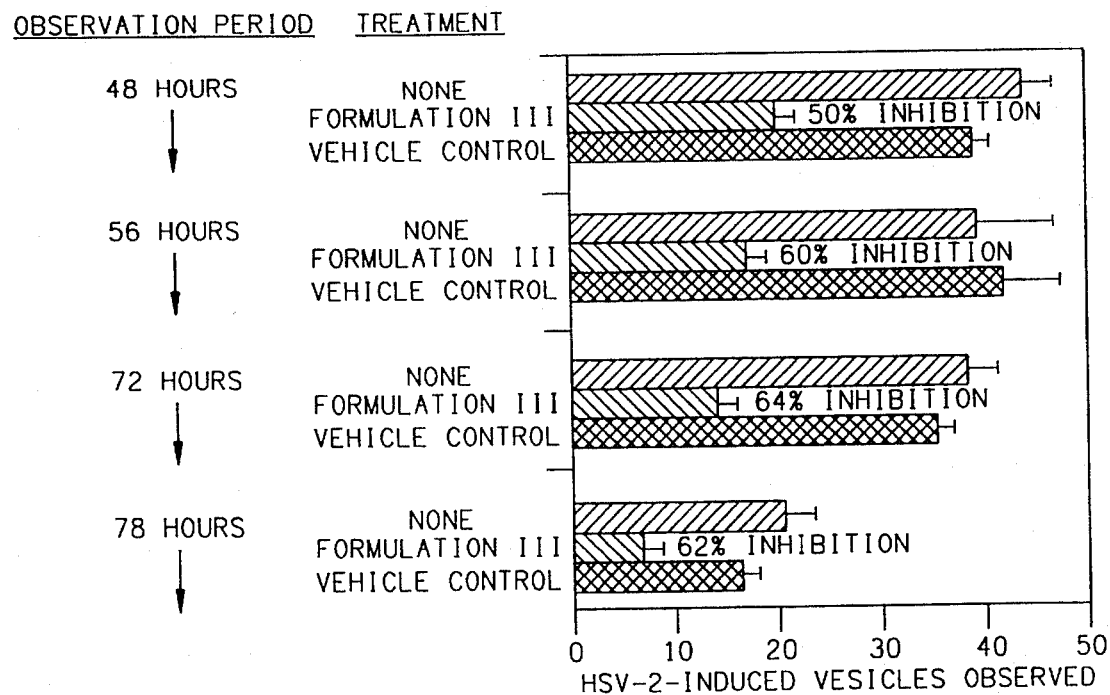

FIG. 5 graphically represents data showing that n-docosanol containing cream based upon a sucrose ester surfactant system (Formulation III) also inhibits HSV-2-induced cutaneous lesions in hairless guinea pigs.

Figure 6A:
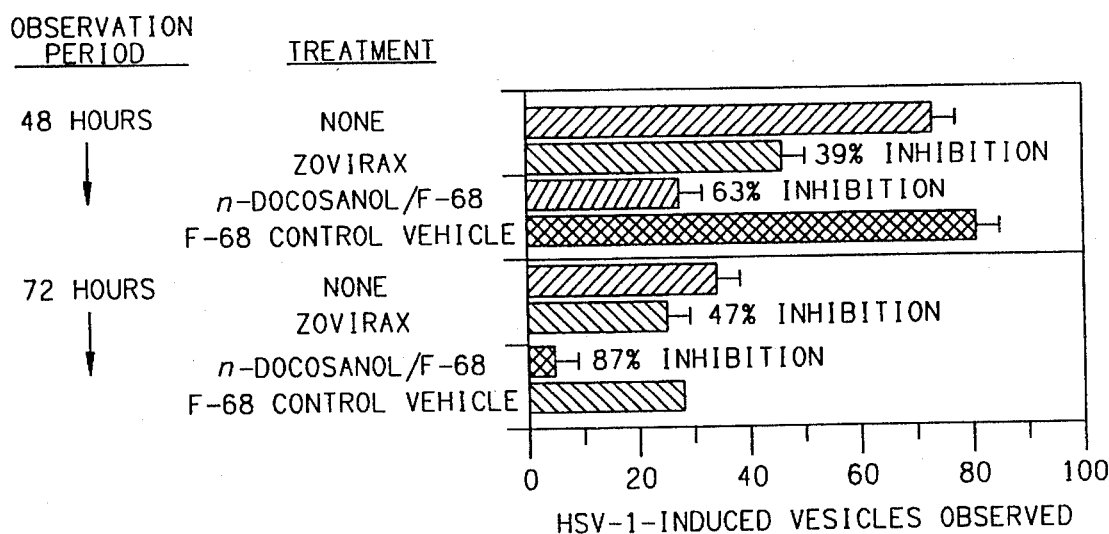

FIG. 6A graphically depicts data that demonstrates that n-docosanol, formulated as a suspension using the surfactant Pluronic F-68, also inhibits HSV-1 induced vesicles when applied before vesicles are present. The suspension formulation did not contain any of the excipients of n-docosanol containing cream including benzyl alcohol.

Figure 6B:
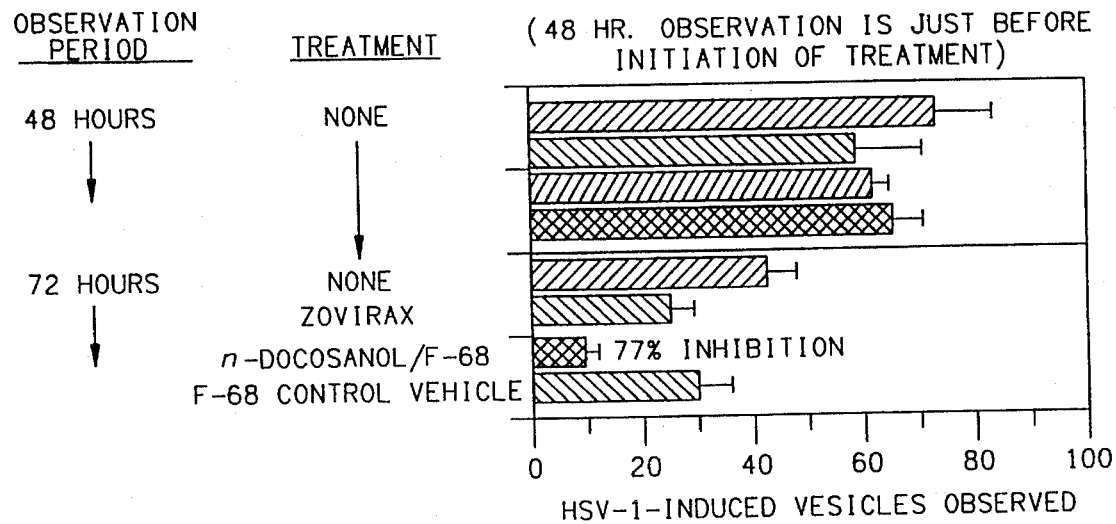

FIG. 6B graphically depicts data that demonstrates that n-docosanol, formulated as a suspension in nonionic surfactant Pluronic F-68, also inhibits HSV-1 induced vesicles when applied after vesicles are present. The suspension formulation did not contain any of the excipients of n-docosanol containing cream including benzyl alcohol.

FIGS. 7 through 13 depict data elucidating the pharmacology of n-docosanol

Figure 7:
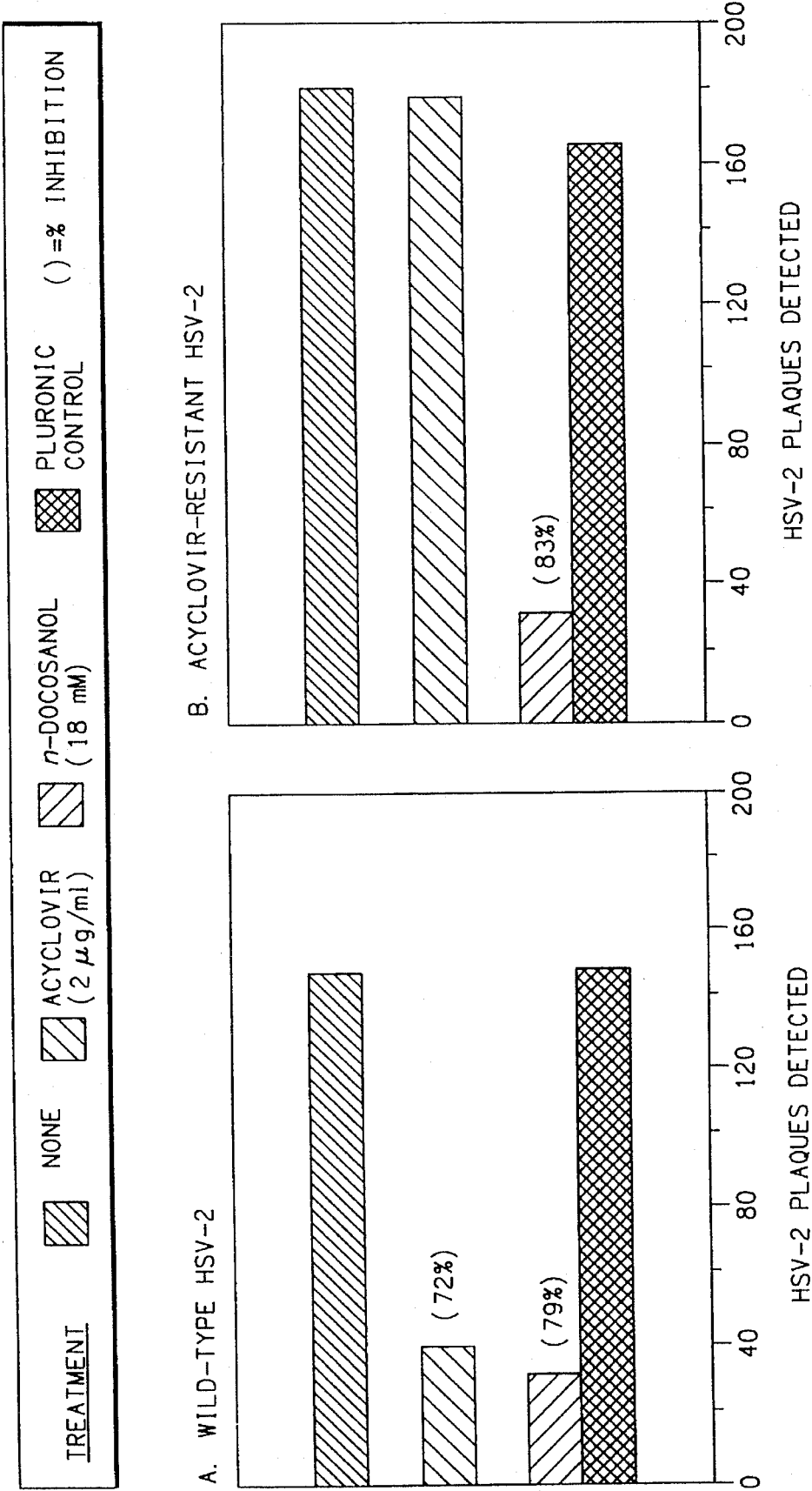

FIG. 7 depicts data showing that n-docosanol inhibits Acyclovir-resistant HSV-2. Veto Cells were cultured in 35-mm wells (6×10$^5$ cells per well) in medium alone (=none) or in the presence of the indicated concentration of acyclovir, n-docosanol-Pluronic F-68 suspension or control suspension (Pluronic F-68 only). The cultures were inoculated 24 hours later with 150 PFU of either wild-type HSV-2 or an acyclovir-resistant laboratory isolate from the wild-type HSV-2 that was plaque-purified and passaged in 20 mg/ml acyclovir 44 hours later, the plates were incubated fixed, stained, and scored for numbers of plaques. The data presented are means of plaques scored from duplicate cultures. The percent inhibition observed in cultures treated with acyclovir or n-docosanol relative to untreated control cultures is denoted in parentheses.

Figure 8:
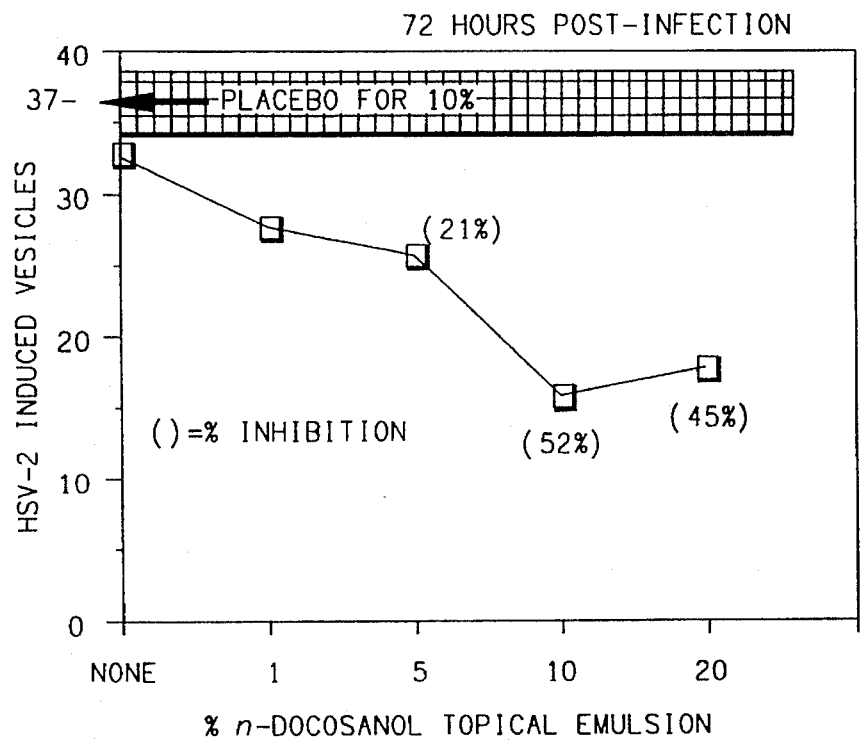

FIG. 8 depicts data showing the dose response of the topical emulsion formulation of n-docosanol on cutaneous HSV in guinea pigs. The backs of hairless guinea pigs were cleaned and inoculated with purified HSV-2 by puncture of the skin with a tattoo instrument. Two hours after virus inoculation, the inoculation sites were either untreated or treated with 100 µl of n-docosanol-containing cream or control vehicle; the sites were similarly treated 24, 30, 48, 52, and 56 hours after virus inoculation. Vesicle number per site was determined at the indicated time points. The data are expressed as means and standard errors of vesicle number derived from duplicate sites per determination. The numbers in parentheses depict percent inhibition of vesicle number at treated sites as compared to the untreated sites.

Figure 9:
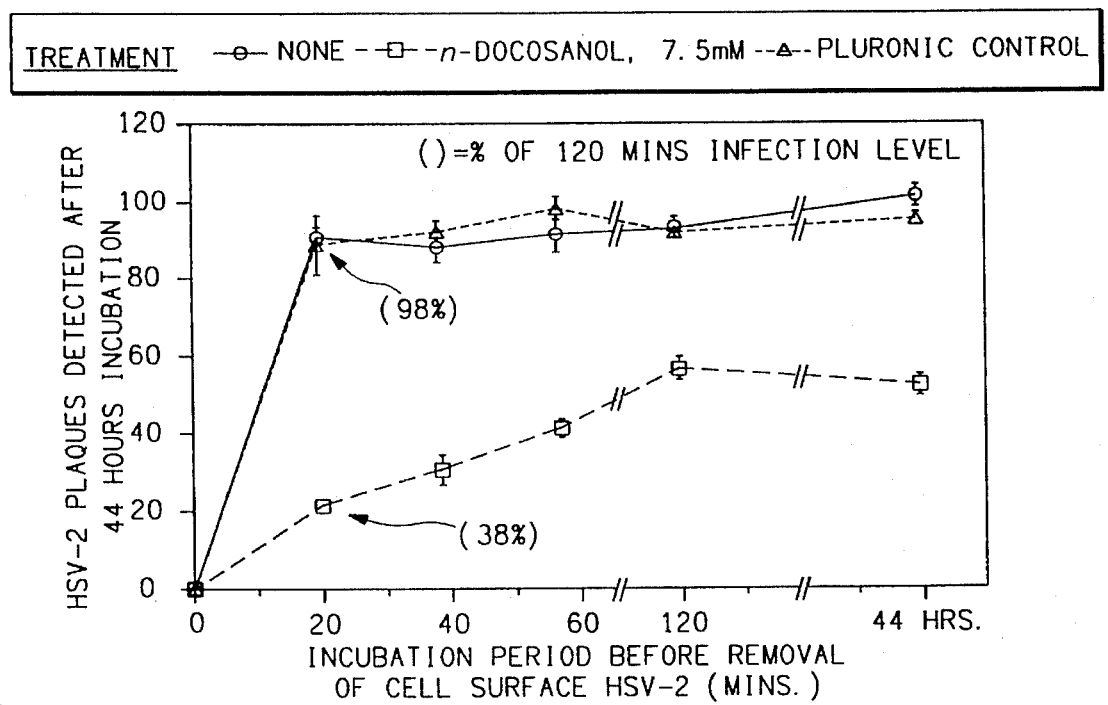

FIG. 9 depicts data showing that HSV-2 remains on the surface of n-docosanol treated Veto cells for prolonged times. Veto cells were cultured as described in the legend to FIG. 7 and incubated overnight. The cultures were then chilled to 4° C., inoculated with 100 PFU of HSV-2, and incubated 3 hours at 4° C. At time zero the cultures were washed with medium, inoculated with fresh medium (containing the indicated inhibitor) and incubated at 37° C. At each indicated time period, the cultures were washed with citrate buffer (pH 2.5) and reinoculated with fresh medium (lacking inhibitor). After a total of 44 hours incubation the cultures were stained and scored for HSV-2-induced plaques. The data are expressed as geometric means and standard errors derived from triplicate cultures per group.

Figure 10:
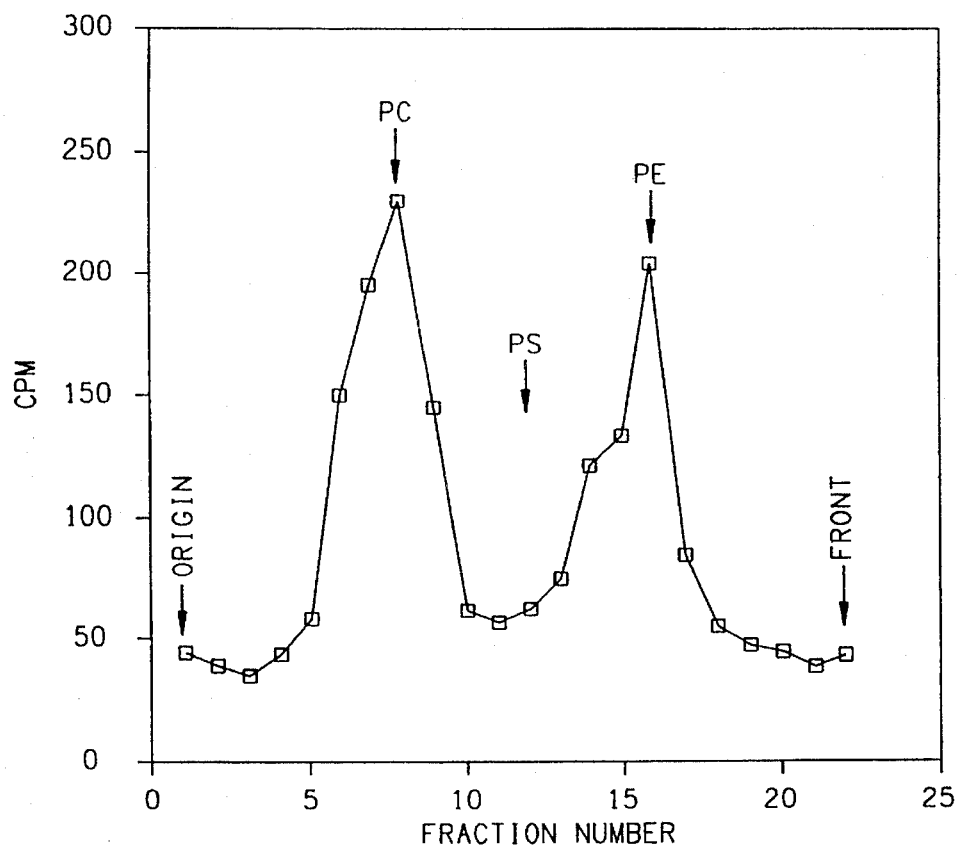

FIG. 10 depicts data showing that radioactive metabolites of n-[$^{14}$C]-docosanol display the properties of phosphatidylcholine and phosphatidylethanolamine. A portion (0.5 ml) of the methanol eluate of the silica lipid fractionation was evaporated under nitrogen, resuspended in 20 ml chloroform:methanol (3:2; v:v) and spotted on a silica thin layer chromatography (TLC) sheet. After development with chloroform:methanol:acetic acid:water (60:50:1:4; v:v:v:v), the positions of standards were determined by staining with iodine vapors and the cpm per fraction determined by scintillation spectrometry after cutting the plastic-backed sheet into 5 mm strips.

Figure 11:
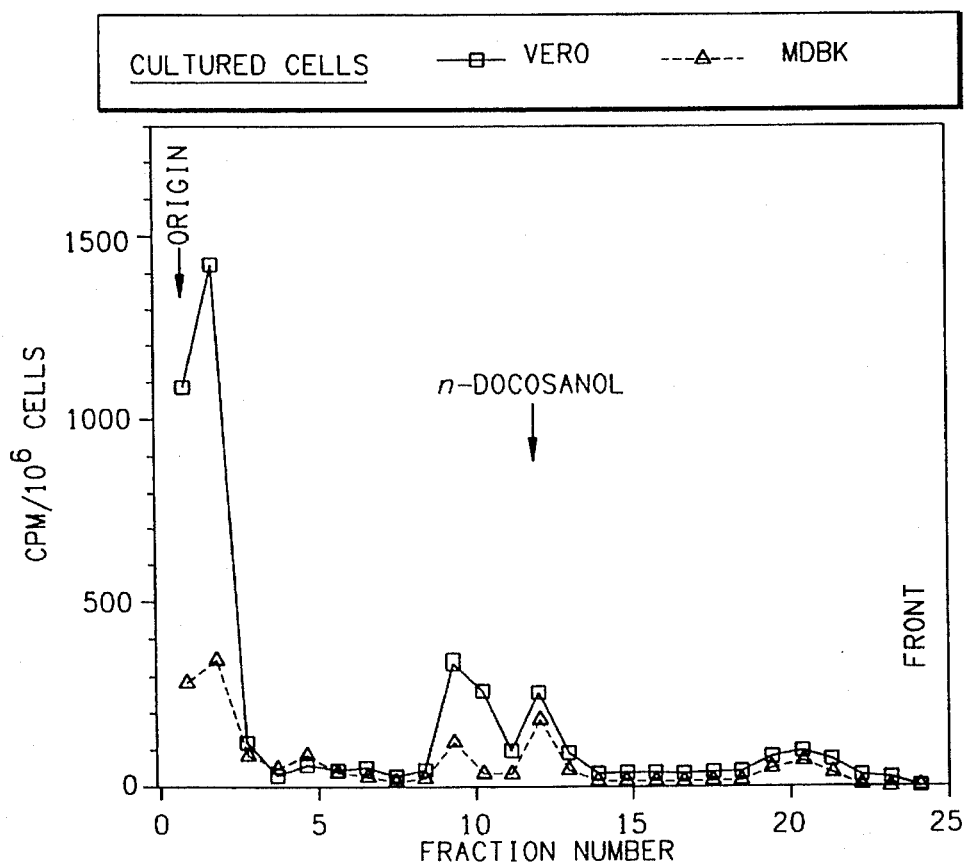

FIG. 11 depicts data showing that n-[$^{14}$C]-docosanol is metabolized more by Vero cells than by MDBK cells. Vero or MDBK cells were plated as described in the specification. n-[$^{14}$C]-Docosanol was added to 6 mM (0.24 mM Tetronic 908) and the cultures were incubated 72 hours at 37° C./CO$_2$. Cells were extracted and analyzed on TLC with hexane:diethyl ether:acetic acid (20:30:1; v:v:v) as the developing solvent. With this solvent system the polar phosphatides remain at the origin. The position of migration of n-docosanol is indicated. Duplicate plates were treated with an identical suspension lacking the radioactive label, and the numbers of cells in these duplicate plates were determined by counting cells excluding trypan blue with a hemocytometer.

FIG. 12 depicts data showing that n-docosanol inhibits in vivo Friend virus-induced leukemia and viremia. Adult B ALB/c mice were injected intravenously with 75 spleen focus-forming units of FV. Treated groups were injected intravenously with the indicated doses of n-docosanol or Pluronic vehicle alone on the same day as virus inoculation and once daily for the next 3 days. After 10 days, half of the animals in each group were sacrificed and examined for leukemic foci in their spleens (panel A). The remaining mice were retained 10 more days and bled for viremia determinations (panel B). Viremia was measured using the X-C plaque assay. Briefly, primary fibroblast cultures were derived by digestion of 14-day BALB/c embryos with trypsin and cultured in DMEM plus 10% fetal calf serum. After 72 hours, the cells were transferred into 16-mm dishes ($10^5$/well), pretreated with 5 μg/ml polybrene and then infected with 75 X-C plaque-forming units of Friend virus stock or dilution of test plasma. After incubation for 7 days, the cultures were irradiated and overlaid with X-C cells ($3\times10^5$/well). Three days later, the cultures were washed, stained and scored for plaques of multinucleated giant cells. The data presented are geometric means and standard errors of splenic foci or X-C plaque-forming units derived from three animals per group.

Figure 13:
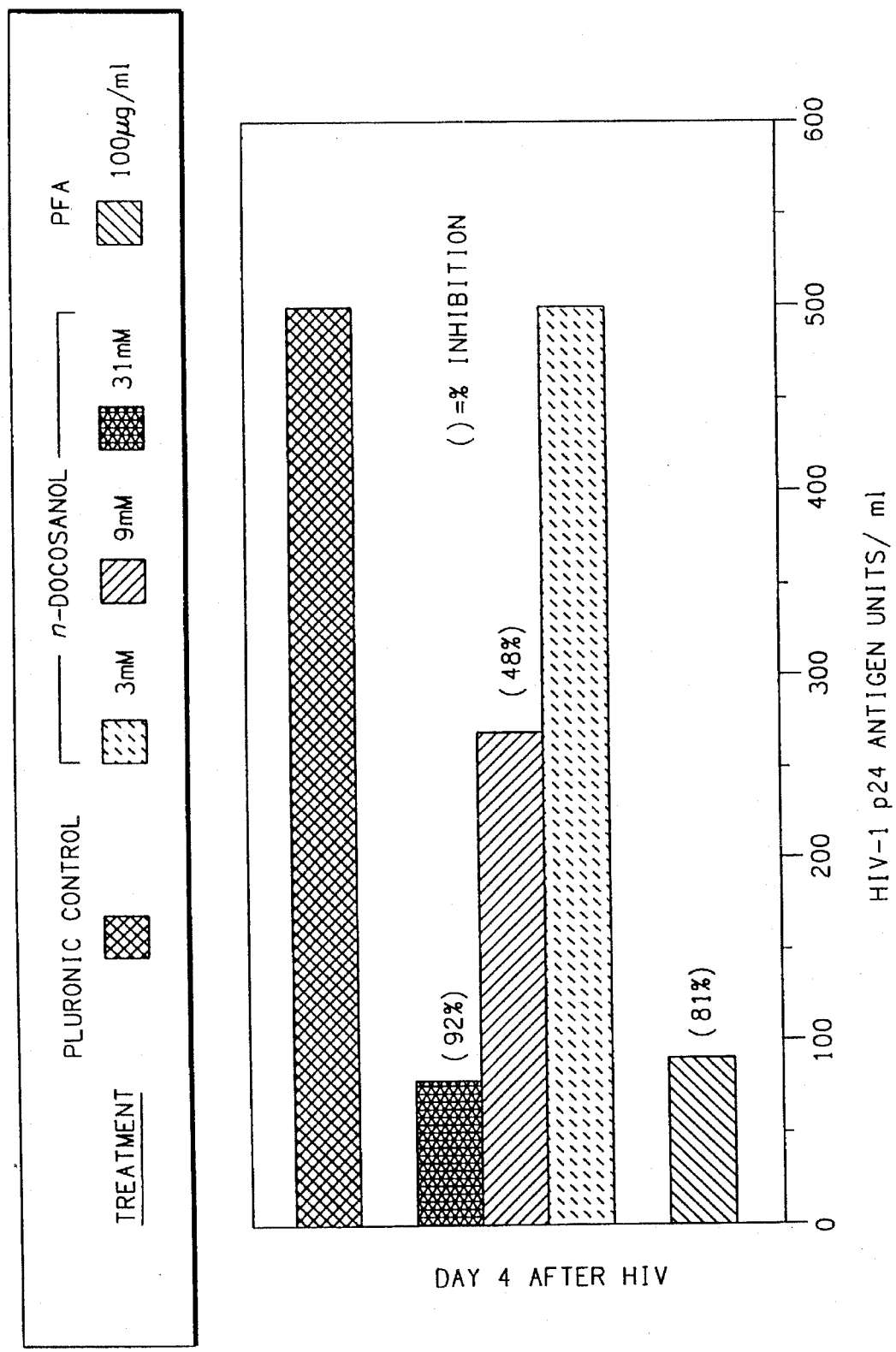

FIG. 13 depicts data showing that n-docosanol inhibits in vitro replication of HIV-1 in cultures of PHA/IL-2-stimulated human peripheral blood mononuclear cells. Human peripheral blood mononuclear cells were cultured in medium containing 1 μg/ml PHA plus 5 units/ml IL-2 alone or also containing 100 μg/ml PFA, the indicated dosage of n-docosanol/Pluronic, or the amount of Pluronic F-68 control vehicle contained in the high dose of n-docosanol/Pluronic. After overnight incubation, the cultures were inoculated with HIV-1 at a multiplicity of infection of 1 virion/cell. After 24 hours incubation at 37° C., the cultures were washed and inoculated with fresh medium containing PHA and IL-2, but lacking inhibitor. Replication of HIV-1 was determined 4 days later by quantitation of viral antigens by a p24-specific ELISA for HIV-1.

DESCRIPTION OF THE PREFERRED EMBODIMENTS

To prepare a cream, n-docosanol (≧98% pure; M. Michel and Co., New York, N.Y.), a water-insoluble compound, is mixed at 80° C. with sucrose cocoate, sucrose stearates, sucrose distearate, mineral oil, propylene glycol and polyoxypropylene-15-stearyl ether. Water was added and mixed in to finish the cream. A cream can also be formed by adding all the materials except n-docosanol to water to form the cream base and blending the n-docosanol into the cream base.

The following proportions were found to be generally optimal:

|  | Suitable Range (% by weight) | Optimum (% by weight) |
| --- | --- | --- |
| n-Docosanol* | 5–25% | 10% |
| Sucrose stearates | 0–15% | 6% |
| Sucrose cocoate | 0–10% | 5% |
| Sucrose distearate | 0–10% | 5% |
| with the proviso that at least one sucrose ester be present and that sucrose ester(s) comprise about 3 weight percent or more, preferably about 10 ± 5 weight percent of the total composition; | | |
| Mineral oil NF | 3–15% | 8% |
| Propylene glycol USP | 2–10% | 5% |
| Polyoxypropylene-15-stearyl ether | 0–5% | 2–3% |
| Benzyl alcohol NF | 0–5% | 2–3% |
| with the proviso that either polyoxypropylene stearyl ether or benzyl alcohol be present in an amount of 2%; | | |
| Purified Water | 40–70% | 55–60% |

*Or at least one long chain aliphatic alcohol having from 20 to 28 carbon atoms, i.e., n-icosanol, n-henicosanol, n-docosanol, n-tricosanol, n-tetracosanol, n-pentacosanol, n-hexacosanol, n-heptacosanol, and n-octacosanol, or mixtures thereof, n-docosanol alone or mixed with such alcohols being exemplary.

A formulation containing 2-ethyl-1,3-hexanediol instead of polyoxpropylene stearyl ether or benzyl alcohol and sucrose esters was also found to be effective but it was felt that some may consider it undesirable to include the compound 2-ethyl-1,3-hexanediol in a composition that was intended for repetitive topical application.

The first formulation of the LIDAKOL (trademark) n-docosanol that showed promise is described in Table 1 below:

TABLE 1

N-DOCOSANOL FORMULATION I

| INGREDIENT | % BY WEIGHT | FUNCTION/RATIONALE |
| --- | --- | --- |
| n-Docosanol | 10.0 | Active drug substance |
| Sucrose Stearates | 11.0 | Emulsifier, Emollient |
| Sucrose Cocoate | 5.0 | Emulsifier, Emollient |
| Mineral Oil NF | 8.0 | Emollient |
| Propylene Glycol USP | 5.0 | Co-solvent, humectant, skin-feel modifier, auxiliary preservative |
| 2-Ethyl-1,3-hexanediol | 2.7 | Co-solvent, auxiliary preservative |
| Purified water qs ad | 58.3 | Vehicle medium |

This was the first n-docosanol cream that was sufficiently stable for more than a short period of time to permit the carrying out of a comprehensive series of animal therapy trials and in which the n-docosanol was found to be consistently active in the animal herpes model (FIGS. 1 through 3) and was used for the initial Phase I human clinical studies which showed it to be safe and tolerable. However, because 2-ethyl-1,3-hexanediol is potentially unacceptable for repetitive use in certain countries outside of the United States, polyoxypropylene-15-stearyl ether was substituted for 2-ethyl-1,3-hexanediol, in equivalent amounts (2.7%), and 5% of the sucrose stearates was replaced with 5% sucrose distearate. The resulting n-docosanol Formulation II composition is described in Table 2, below:

TABLE 2

N-DOCOSANOL FORMULATION II

| INGREDIENT | % BY WEIGHT | FUNCTION/RATIONALE |
| --- | --- | --- |
| n-Docosanol | 10.0 | Active drug substance |
| Sucrose Stearates | 6.0 | Emulsifier, Emollient |
| Sucrose Cocoate | 5.0 | Emulsifier, Emollient |
| Sucrose Distearate | 5.0 | Emulsifier, Emollient |
| Mineral Oil NF | 8.0 | Emollient |
| Propylene Glycol USP | 5.0 | Co-solvent, humectant, skin-feel modifier, auxiliary preservative |
| Polyoxypropylene-15-Stearyl Ether | 2.7 | Co-solvent, auxiliary preservative |
| Purified water qs ad | 58.3 | Vehicle medium |

This modified Formulation II succeeded in replacing ethyl-hexanediol and providing physical stability to the final drug product and performed well in the guinea pig herpes animal model (see FIGS. 1 and 2). However, this formulation failed the USP preservative effectiveness test and, therefore, was deemed unsuitable for human clinical application. This microbiological instability was solved by replacing polyoxypropylene-15-stearyl ether with benzyl alcohol as co-solvent excipient, as described below.

It was found that the use of only one or two surfactants of the classes described and that the use of surfactants in amounts of about 5% resulted in a stable composition. The ability to use only one or two types of surfactants and the use of lower amounts of surfactant to produce stable creams was an unexpected and desirable result of our laboratory work. Excessive surfactant is not desirable because excess surfactant increases the potential for irritation at levels of surfactants above 5%. In addition, formulations with excessive amounts of nonionic surfactants frequently have problems with preservative effectiveness (which may have contributed to the microbiological instability problems of Formulation II).

Utilizing several surfactant blends, with hydrophilic-lypophilic balance (HLB) values ranging from 9.0 to 13.0, a variety of n-docosanol creams were formulated and then screened for optimal emulsion quality, physical characteristics, drug efficacy and accelerated physical stability. Although most pharmaceutical emulsions are based on binary surfactant blends to optimize the HLB, this program revealed that sucrose stearates alone performs as well as or better than any surfactant blends in the improved n-docosanol formula. The composition of this improved n-docosanol formula (Formulation III) is as follows:

a well-known preservative and co-solvent with a long history of safe use and compendial status. The liquid nature and like functions of benzyl alcohol make it a rational and low risk replacement for ethyl hexanediol. The total surfactant level was reduced to 5% active with no change in the pharmaceutical characteristics of the product, no negative effect on the quality of emulsion based on microscopic examination, and no loss of physical stability in accelerated testing. Sucrose cocoate was found to be unnecessary, and was omitted.

The cream can be made by the original order of heating and addition of ingredients, or by a preferred method of combining oil-soluble ingredients and heating them separately from the water soluble components. The hot oil-soluble components are then added to the hot water phase while mixing vigorously.

Table 4 summarizes the most significant of the formulations evaluated.

TABLE 3

N-DOCOSANOL (FORMULATION III)

| INGREDIENT | % BY WEIGHT | FUNCTION/RATIONALE |
| --- | --- | --- |
| n-Docosanol | 10.0 | Active drug substance |
| Sucrose Stearates | 5.0 | Emulsifier, Emollient |
| Mineral Oil NF | 8.0 | Emollient |
| Propylene Glycol USP | 5.0 | Co-solvent, humectant, skin-feel modifier, auxiliary preservative |
| Benzyl Alcohol NF | 2.7 | Co-solvent, auxiliary preservative |
| Purified water qs ad | 69.3 | Vehicle medium |

The changes in the improved Formulation III as compared with the original formulation (Formulation I) include the replacement of 2-ethyl-1,3-hexanediol with benzyl alcohol,

TABLE 4

| | FORMULATIONS (% COMPOSITION) | | | | |
|---|---|---|---|---|---|
| INGREDIENTS | I | III | IA | III | FUNCTION/RATIONALE |
| n-Docosanol | 10.0 | 10.0 | 10.0 | 10.0 | Active Drug Substance. |
| Sucrose Stearates | 11.0 | 6.0 | 11.0 | 5.0 | Emulsifier, emollient. |
| Sucrose Cocoate | 5.0 | 5.0 | 5.0 | — | Emulsifier, emollient. |
| Sucrose Distearate | — | 5.0 | — | — | Emulsifier, emollient. |
| Mneral Oil NF | 8.0 | 9.0 | 8.0 | 8.0 | Emollient. |
| Propylene Glycol | 5.0 | 5.0 | 5.0 | 5.0 | Co-solvent, auxiliary preservative. |
| 2-Ethyl-1,3-hexanediol | 2.7 | — | — | — | Co-solvent, auxiliary preservative. |
| Polyoxy-propylene-15-stearyl ether | — | 2.7 | — | — | Co-solvent, auxiliary preservative. |
| Benzyl Alcohol NF | — | — | 2.7 | 2.7 | Co-solvent, preservative |
| Water | 58.3 | 58.3 | 58.3 | 69.3 | Vehicle medium. |

The improved n-docosanol Formulation III passed accelerated physical stability screening (storage at 42°; freeze-thaw cycles) and also passed the USP preservative effectiveness test. Drug efficacy in the guinea pig herpes model was verified on repeated occasions.

To monitor the stability, the n-docosanol cream formulations were stored, variously, at room temperature (30° C.), at elevated temperature (42° C.) and under freeze-thaw conditions in polypropylene jars. The freeze-thaw samples were subjected to 48 hours of freeze-thaw cycles, i.e., 24 hours at freezing temperature (−15° C.) and 24 hours at ambient room temperature. The cream samples, stored under the respective conditions, were visually inspected for physical stability at various time points. After 12 months at 30° C. or 3 months at 42° C. or 24 freeze-thaw cycles all samples remained as off-white creams. There was no evidence of syneresis or phase separation. Based on the above visual inspection, the Formulation III of 10% n-docosanol cream was considered to be physically stable when stored under any of the stated conditions.

The exact shelf-life of Formulation HI has not been determined but experience suggests that shelf-life is more than adequate for a commercial n-docosanol containing cream.

To confirm in an experimental animal model the efficacy of n-docosanol cream on HSV-induced lesions, and to compare its activity to that of ZOVIRAX, hairless guinea pigs were inoculated with $1 \times 10^6$ PFU of HSV-1, and then treated with either n-docosanol-containing or control cream, or ZOVIRAX ointment. The n-docosanol creams were constructed as described. The control cream was constructed in a similar manner except stearic acid was substituted for n-docosanol. Treatment was started either 2 or 48 hours after virus inoculation. The sites were evaluated for vesicle formation, defined as a pus-filled blister, at the indicated time points.

FIG. 1 presents the comparative activities of Formulation I and three different preparations of Formulation II as well as ZOVIRAX. Formulation I and Formulation II of n-docosanol creams both showed greater inhibitory power than ZOVIRAX ointment.

FIG. 2 presents the comparative activities of Formulation I, Formulation IA and Formulation II. Significant inhibition of HSV-1-induced lesions was demonstrated for all three formulations.

FIG. 3 shows a comparison of activities of Formulation III versus Formulation I and also depicts certain modifications of these formulations in which the relative surfactant concentrations have been modified from that of Formulation I. Modifications of surfactant concentrations were found to have appreciable deleterious effects on the extent of drug activity. Formulation III was shown to have potent inhibitory power for HSV-1-induced lesions.

Volunteer patients with recurrent oral or genital HSV I or II infections have also been treated with topical n-docosanol-containing cream at various stages of an acute herpes outbreak. When treatment is initiated during the prodromal stage, n-docosanol cream generally aborts further progression of the infection (i.e., prevents vesicle formation). When treatment is started after vesicle formation has already occurred, n-docosanol cream substantially shortens (e.g., by 50% or more) the time for healing (i.e., complete re-epithelialization) of such herpes lesions. In over 100 oral and genital patient episodes which have been treated thus far, therapeutic efficacy of greater than 95% was observed.

Thus, while most n-docosanol formulations are unstable, specific formulations, Formulation III being preferred, have been found to be both stable and efficacious.

The selection of 10% n-docosanol in the formulation was justified by a dose-response study in the hairless guinea pigs. The sites on the backs of hairless guinea pigs were inoculated with HSV-2 as described previously. The sites were treated with 1%, 5%, 10% and 20% n-docosanol formulations. A vehicle control containing no n-docosanol was also included in the study. The results, illustrated in FIG. 4, show that after 72 hours of virus inoculation the untreated sites exhibited an average of 41 vesicles. Treatment with 20% and 10% n-docosanol containing cream inhibited vesicle number by 50% and 60%, respectively. Creams containing 1% and 5% n-docosanol were less effective than the 10% preparation. The control vehicle was without appreciable inhibitory effect.

Those skilled in the an of formulating creams of hydrophobic and hydrophilic compounds will recognize that certain substitutions will be available. Glycerol or another glycol could be used, with some adjustments in ratios, in place of propylene glycol, for example. Other polyoxyalkylene-based ethers may also be found to be substitutable for polyoxypropylene-15-stearyl ether. The relative proportions of the sugar-based esters may be varied considerably, so long as the total amount of sugar-based ester present is sufficient to stabilize the n-docosanol. This amount is believed to be from about 5% to about 25% by weight, though the minimum and maximum amounts have not been determined with precision.

The current preferred formulation for n-docosanol cream is Formulation III containing 10% n-docosanol, 5% sucrose stearates, 8% mineral oil NF, 5% propylene glycol USP, 2.7% benzyl alcohol NF and 69.3% purified water.

Since it was reported that benzyl alcohol had some antiviral activity under certain circumstances, (Farah, A. E. et al, U.S. Pat. No. 4,200,655) the formulation of this invention was tested to determine if benzyl alcohol acts as an antiviral reagent in the formulation. The cream containing benzyl alcohol and n-docosanol (10% n-docosanol cream) and the cream containing benzyl alcohol alone (placebo) were tested on HSV-2 induced cutaneous lesions in the hairless guinea pigs. Sites on the backs of guinea pigs were inoculated with HSV-2. The sites were treated as indicated in FIG. 5 and evaluated for vesicle formation at 48, 56, 72 and 78 hours after virus inoculation. There was an average of 44 vesicles in the untreated sites at the 48-hour time point, which remained relatively constant up to 72 hours after infection. At the 78-hour time point, resolution of the lesions became evident and by 96 hours post-inoculation vesicles were no longer visible. Treatment with n-docosanol cream inhibited vesicle number by 50–60% at the 48–56-hour time points, and by a slightly higher amount at the 72–78-hour points of analysis. Treatment with the control vehicle was without appreciable effect on vesicle number at any time point. Untreated and treated sites were excised and processed for viral culture. The presence of vesicles was directly correlated with the presence of infectious virus regardless of treatment or time of assay (not shown). Thus, vesicle number is an appropriate indicator for disease state in the studies described herein. Additionally, the cream and the placebo were tested in a phase II pilot study comprising 68 patients with herpes labialis. The result of the double blind trial showed that early application of n-docosanol cream cut the duration of the episodes nearly in half The treated groups' average outbreak period was 3.4 days, while the placebo group had outbreaks averaging 6.6 days. Above results show that the presence of n-docosanol in the formulation is necessary for significant antiviral action.

The antiviral activity of n-docosanol has also been demonstrated in a suspension formulation of n-docosanol in the nonionic surfactant Pluronic F-68 which did not contain any of the excipients of 10% n-docosanol cream formulation including benzyl alcohol. The results, summarized in FIG. 6 demonstrate two important points. First, as shown in panel A, a suspension formulation of n-docosanol in Pluronic F-68 also inhibits HSV-1 induced vesicles when applied 2 hours after virus infection, as observed with the cream formulation. Thus, the untreated sites exhibited an average of 74 vesicles at 48 hours after virus, but only 28 vesicles were observed in the sites treated with n-docosanol/F-68 (63% inhibition). Treatment with ZOVIRAX, the current treatment of choice for HSV infections in humans, was also associated with decreased vesicle number, but less so than with n-docosanol. Continued treatment with n-docosanol resulted in many fewer vesicles at the 72 hour time point also. The vehicle control for the n-docosanol preparation was without effect at either time point.

The second major point derived from FIG. 6 is that n-docosanol hastens resolution of HSV-1 induced disease even when administered after vesicles have emerged (Panel B). The various sites exhibited roughly equivalent number of vesicles at the 48-hour time point, which would be expected since none had been treated by that time. Vesicle numbers decreased in the untreated sites from a mean of 73 vesicles at 48 hours to 43 vesicles at 72 hours. Treatment with ZOVIRAX was associated with a modestly hastened disease resolution at 72 hours (27 vesicles, a 37% decrease versus the untreated sites), which is consistent with other experiments of a similar design. Importantly, application of n-docosanol/F-68 significantly hastened vesicle resolution as shown by the 77% inhibition of vesicle number when compared with the untreated group. The same conclusions were obtained using the cream formulation in experiments of a similar design. This demonstrates that n-docosanol need not be administered prophylactically to alter the HSV-induced course of disease.

Three safety and tolerance studies were conducted in healthy Caucasian male and female volunteers. A total of 78 healthy volunteers were exposed to drug. The safety studies indicated that the formulation of n-docosanol 10% cream does not appear to cause phototoxicity, but is a mild primary irritant which also has the potential, albeit in low incidence, to cause allergic sensitization (1 subject of the 78 exposed experienced contact dermatitis).

Two clinical efficacy studies have been completed. Study A was a randomized, double-blind, placebo-controlled Phase 2 study in 63 patients (male and female) with recurrent herpes labialis. All of the 31 n-docosanol 10% cream-treated patients in the herpes labialis study, Study A, completed their treatment; 2 of those 31 patients reported a burning or stinging sensation after application of the cream. No clinically significant changes in clinical laboratory values (blood chemistry, hematology, and urine analysis) were revealed in either study. Study B was a randomized, double-blind, placebo-controlled trial in 44 female patients with recurrent herpes genitalis. All of the 22 n-docosanol 10% cream-treated patients in the genital study, Study B, completed their treatment without reporting any drug-related adverse events.

Study A

Sixty five patients (aged 18–60) took part in the Study A, 32 patients were initially randomized to receive 10% n-docosanol cream and 33 were initially randomized to receive placebo cream. Treatment was patient-initiated, and treatment initiation was defined as 'early' if the treatment started at prodrome or erythema stage and as 'late' if started at the papule stage or later. Two patients were excluded from the analysis. Of the 63 evaluable patients, 22 were entered into the cross-over phase of the study. In addition, 13 patients treated more than one episode with the same study medication. Therefore, a total of 98 herpes episodes—48 treated with 10% n-docosanol cream and 50 treated with placebo cream—were analyzed.

The results of Study A are summarized according to first treatment episodes, cross-over treatments and all treatment episodes combined in Table 5.

TABLE 5

STUDY A: TIME TO HEALING (DAYS) OF RECURRENT HERPES LABIALIS EPISODES

| | n-DOCOSANOL 10% | | | PLACEBO | | |
|---|---|---|---|---|---|---|
| | MEAN | SD | (n) | MEAN | SD | (n) |
| Part A. Analysis of first episodes | | | | | | |
| Early treatment | 2.5 | 2.4 | (10) | 6.8 | 4.2 | (4) |
| Late treatment | 6.8 | 3.2 | (21) | 7.3 | 2.7 | (29) |
| All treatments | 5.4 | 3.6 | (31) | 7.3 | 2.8 | (32) |

TABLE 5-continued

STUDY A: TIME TO HEALING (DAYS) OF
RECURRENT HERPES LABIALIS EPISODES

| | n-DOCOSANOL 10% | | | PLACEBO | | |
|---|---|---|---|---|---|---|
| | MEAN | SD | (n) | MEAN | SD | (n) |
| Part B. Analysis of cross-over study | | | | | | |
| Early treatment | 2.7 | 2.2 | (7) | 7.0 | | (1) |
| Late treatment | 5.6 | 2.1 | (15) | 8.0 | 2.6 | (21) |
| All treatments | 4.7 | 2.5 | (22) | 8.0 | 2.5 | (22) |
| Part C. Analysis of all treatment episodes in the study | | | | | | |
| Early treatment | 3.4 | 3.0 | (13) | 6.7 | 3.9 | (7) |
| Late treatment | 6.5 | 2;7 | (35) | 7.4 | 2.7 | (43) |
| All treatments | 5.7 | 3.1 | (48) | 7.3 | 2.9 | (50) |

Thirty-one (31) patients treated their first episode of herpes labialis with 10% n-docosanol and 32 with placebo (Part A). Ten patients in the n-docosanol group and 4 in the placebo group were classified as early treatments. Mean healing time in the early-treatment n-docosanol group was 2.5 days, a reduction in mean healing time of 4.3–4.8 days compared with the other treatment modalities. This difference was statistically highly significant (P=0.0001) in favor of n-docosanol. In the late treatment cohort, n-docosanol reduced mean healing time in the first episodes by 0.5 day, which was not statistically significant.

Of the 22 patients entered into the cross-over study, the number who had treated their lesions early in both parts of the study (7 using n-docosanol in the cross-over phase and 1 using placebo) was too small for meaningful statistical analysis (Part B). However, a substantial number (15 using n-docosanol in the cross-over phase and 21 using placebo) had treated their lesions late, thus allowing for intra-patient comparison in this respect. Analysis of variance of the results of late treatment revealed a significant difference in favor of n-docosanol (P=0.03).

Evaluating the data from all 98 treatment episodes of Study A together (single episodes, cross-over episodes and additional episodes with the same medication) reveals a statistically significant (P=0.02) reduction in mean overall healing time of 1.6 days in n-docosanol-treated (5.7 days) versus placebo-treated (7.3 days) patients (Part C). In the total 20 episodes classified as early treatments, topical n-docosanol reduced mean healing time by 3.3 days (P=0.05). Finally, when effectiveness of early treatment with n-docosanol was compared to all other treatment modalities, mean healing time in the early treatment n-docosanol group (3.4 days) differed quite significantly from the range of 6.5 to 7.4 days in the other groups; this difference was highly significant in favor of n-docosanol (P=0.0002). The differences between late treatment with n-docosanol 10% and early and late placebo treatment were not significant.

As demonstrated by the data summarized in Table 5, early treatment with 10% n-docosanol cream (in the prodromal or erythema stage) produced a highly significant shortening of healing time compared with that obtained with the other treatments. In addition, late treatment, started after lesions had appeared, resulted in a statistically significant reduction in healing time in the n-docosanol-treated group in the cross-over portion of the study, though not in the other analyses.

Study B

In the first clinical study, sixty female patients with recurrent herpes genitalis entered the study while symptom-free and not in a prodromal stage. Thirty subjects were initially randomized to receive 10% n-docosanol cream and 30 to receive placebo cream in this patient-initiated trial for the treatment of early-stage herpes genitalis recurrences. Forty-four patients initiated treatment and returned to the clinic with a herpetic episode; 22 of these patients received n-docosanol and 22 received placebo.

The mean time to healing in the 16 evaluable n-docosanol patients was 4.7 days±1.9, ranging from 1.8 to 8.6 days; for the 18 evaluable placebo patients, healing was complete within a mean of 5.1 days±2.3, ranging from 1.7 to 10.4 days. The difference was not statistically significant (p=0.5827, t-test). Patients with non genital lesions, who were noncompliant or had dosing interruptions, who had prodrome with no observable episode, or who had concurrent yeast infection, were considered nonevaluable. When all patients are included, the mean time to healing of the n-docosanol group was 5.5 days±2.5, ranging from 1.8 to 9.8 days. For the placebo group, healing was achieved in a mean of 4.7 days±2.3. Healing time in this group ranged from 1.7 to 10.4 days. There was no statistically significant difference in the mean time to healing between the 2 treatment groups (p=0.2703, t-test). There was also no statistically significant difference between treatment groups when patients were stratified according to stage of the lesions (prodrome, erythema, or papule) when the treatment was initiated. The average healing time based on patient ratings was similar to the clinicians' (5.6 days for all n-docosanol patients versus 4.5 for all placebo patients).

Three pain analyses were conducted, based on patients' self-assessment of pain: time to sustained "no pain"; time to first "no pain"; and time to first reduction of pain. Time to sustained "no pain" was measured from the time of first pain at application to the time when 1) pain was scored as "no pain" for a minimum of 2 consecutive recordings; and 2) during the remainder of the episode, additional pain recordings were no more frequent and severe than 2 separated episodes of 2 consecutive recordings of "mild" pain. Time to first "no pain" was defined as the interval from first pain at application to the first recording of "no pain". Time to first reduction in pain was measured from the time of first pain at application to the first time when a decrease in pain level was noted, relative to the previous assessment. Several patients were excluded from these analyses because of either lack of pain within the first 24 hours, or noncompliance in reporting pain.

The 15 evaluable patients treated with n-docosanol achieved a sustained response of "no pain" sooner than the 14 evaluable placebo patients: a mean of 3.2 days ±1.9 for n-docosanol patients compared to 4.1 days±2.5 for placebo patients. The n-docosanol patients also achieved "no pain" sooner than the placebo patients. The n-docosanol patients first recorded "no pain" a mean of 2.6 days±2.1 after pain onset, while the placebo patients first reported "no pain" a mean of 3.4 days±2.1 after pain onset. Among the evaluable n-docosanol patients, the first reduction in pain, relative to pain at the preceding application, occurred at a mean of 1.2 days±1.0 after pain onset. First reduction in pain occurred in the placebo patients at a mean of 1.8 days±1.4. These differences were not statistically significant (p=0.2775, 0.325, and 0.1757, respectively, t-test). Patients with non-genital lesions, who were noncompliant or had dosing interruptions, prodrome with no observable episode, and concurrent yeast infection, were considered nonevaluable.

The invention, according to the surprising discovery that it is an effective topical pain relieving agent, comprises a method of reducing the pain of a surface inflammation of the skin or membrane comprising applying to the inflamed surface a composition of at least one long chain aliphatic alcohol having from 20 to 28 carbon atoms selected from the group consisting of n-icosanol, n-henicosanol, n-docosanol, n-tricosanol, n-tetracosanol, n-pentacosanol, n-hexacosanol, n-heptacosanol, and n-octacosanol, or mixtures thereof, in a physiologically compatible carrier, said alcohol comprising from about 5% to about 25% by weight of said composition. Preferably, the physiologically compatible carrier is a cream base that comprises one or more compounds selected from the group consisting of sucrose cocoate, sucrose stearates and sucrose distearate and one or more compounds selected from the group consisting of polyoxypropylene stearyl ether ethyl hexanediol and benzyl alcohol.

While no statistically significant differences were noted in Study B in time-to-healing between patients who received 10% n-docosanol cream and those who received placebo cream, although there was a trend towards reduced time-to-healing among the evaluable patients treated with n-docosanol. Three different pain analyses all showed a more rapid resolution of pain in the subjects who received n-docosanol 10% cream, though none of the differences were statistically significant. The inability to detect statistical significance in this study may reflect, in part, (1) the small study population; (2) differences at study entry, between the two study groups with respect to the natural history of herpes genitalis lesions; and (3) an unequal distribution between the two groups of lesional stage at episode and treatment initiation. In addition to the clinical studies, several studies were carried out to elucidate the pharmacology of n-docosanol. These studies resulted in the data depicted in FIGS. 7 through 13, and discussed below.

One of the more difficult hurdles to overcome in order to study the biological activity of n-docosanol was the development of an appropriate formulation which allowed acceptable delivery of the compound to biological systems. Initially, this was accomplished by formulating a suspension of the hydrophobic molecule in the inert and nontoxic nonionic surfactant, Pluronic F-68. Such suspensions proved to be homogeneous in quality, consisting of n-docosanol containing particles averaging 0.10 microns in size. Suspended in this way n-docosanol exerts excellent inhibitory activity in vitro against both type 1 and 2 Herpes simplex virus (HSV) infectivity of both simian and human cell lines. Significantly, n-docosanol/Pluronic suspensions are equally effective against both wild-type and acyclovir-resistant mutants of HSV. Thus, as shown in FIG. 7, Panel A, both acyclovir and n-docosanol inhibit plaque formation by wild type HSV-2 equally. FIG. 7, Panel B illustrates that an acyclovir-resistant HSV-2 mutant fails to respond to acyclovir, as expected, but is very clearly susceptible to the inhibitory activity of n-docosanol. The last bar in both panels illustrates that the Pluronic surfactant alone lacks any antiviral activity. Host cell toxicity was not observed even with 300 mM n-docosanol.

The apparently very high doses of n-docosanol used in these tissue culture studies deserves special comment. This is actually an artifact of the in vitro system, and is due to limited delivery of the molecule from the particulate suspension to the adherent cells. Transfer may be limited for several reasons. First, the density of this type of suspension causes most of the particles to float upwards. Consequently, there is a physicochemical artifact created in the tissue culture well which requires high peripheral quantities of the suspended drug in order to obtain the fluid dynamic gradient required to deliver the bioactive dose to the attached target cell monolayer. Second, transfer of molecules of n-docosanol from thermodynamically stable particles to cultured cells would not be expected to be an efficient process. As shown by the uptake studies, the actual bioactive dose of n-docosanol in these cultures is 1/1000 of the dose shown in FIGS. 7 and 9; in effect one can simply translate the number shown in mM to µM.

Antiviral activity in a tissue culture system does not always translate into drug efficacy in whole animal studies or in man. Therefore, we examined the activity of the topical emulsion for human use (which was specifically designed to maximize skin penetration and minimize potential local irritation reactions) in the treatment of HSV-induced cutaneous lesions in guinea pigs. HSV-1 or -2 was inoculated with a tattoo instrument into the skin on the backs of hairless guinea pigs. The sites were either left untreated or treated with varying concentrations of n-docosanol-containing cream or the control vehicle. Treatment was applied 2 hours after inoculation and again at 24, 36 and 48 hours. Vesicle formation was enumerated at the inoculation sites at the 56- and 72-hour time points after inoculation, representing peak and resolution phases, respectively, of the disease. The data shown in FIG. 8 illustrates a dose-response study testing concentrations of 1%, 5%, 10% and 20% n-docosanol creams for inhibition of HSV-2-induced lesions in hairless guinea pig skin. The placebo corresponding to the 10% n-docosanol-containing preparation was included in this experiment and the data obtained with that placebo is illustrated at the top of the line graph in the horizontal column with the data point denoted by the arrow. Only the data for the 72-hour time point is shown, but a similar pattern of inhibition was observed at earlier times. As shown, this topical formulation of n-docosanol exerts good antiviral activity; optimal inhibitory activity was obtained with the 10% cream (60% inhibition), and essentially comparable activity was observed with the 20% preparation. The somewhat lower inhibitory activity of the 20% cream is a consistent observation and most likely relates to saturation of the surfactants by the hydrophobic n-docosanol molecule as evidenced by the longer time required to achieve disappearance of the cream into the skin (not shown). Creams containing 5% and 1% n-docosanol were clearly less effective than the 10% preparation, and the placebo corresponding to the 10% cream had absolutely no activity. Although not shown, comparable results have been obtained with HSV-1-induced cutaneous lesions in this hairless guinea pig model. Thus, 10% n-docosanol cream is effective in reducing HSV-induced cutaneous lesions in guinea pigs.

Extensive studies designed to delineate the mechanism by which n-docosanol exerts its antiviral activity were conducted. The collective implications of the results of the studies are that the compound appears to interfere with one or more of the common pathways of viral entry into the cell and migration to the nucleus of infected target cells. The key points of evidence supporting this notion can be summarized as follows: (a) the compound has no direct virucidal activity, since virus can be mixed with a n-docosanol suspension, then recovered from the suspension and shown to retain normal infectivity; (b) although the compound does not interfere with binding of herpes virus to HSV-specific receptors on target cells, HSV virions which have bound to target cell receptors in the presence of n-docosanol remain on the cell surface for a prolonged time period; and (c) subsequent migration to the cell nucleus of virus which has been internalized is significantly inhibited, as measured by detectable HSV core and envelope protein, numbers of cells expressing the immediate early protein, ICP-4, and secondary plaque assays.

The delay in virus internalization described above is illustrated in the experiment summarized in FIG. 9. In this experiment, HSV-2 was incubated with Vero cells in the absence or presence of n-docosanol at 4° C. to allow for receptor binding of the virus. At the end of 3 hours, all cultures were washed and then replated at 37° C. in order to initiate the viral entry process. At 20 minute intervals thereafter, the various cultures were exposed to pH 3.0 citrate buffer under conditions which remove and inactivate surface-bound, but not internalized, HSV virions, and then re-cultured the full 44 hour period required to develop optimal HSV plaques. All cultures exposed to citrate buffer at time-0 failed to develop plaques, as expected. As shown by the uppermost lines on the graph, internalization of HSV-2 is virtually complete within 20 minutes after the shift to 37° C. in the untreated and Pluronic control-treated cultures. In contrast, internalization of HSV in the n-docosanol treated cultures was less than 40% complete by 20 minutes and required more than 1 hour to reach completion. These results clearly indicate that the kinetics of viral fusion and/or transmembrane migration are delayed in some way by n-docosanol.

Even after internalization reaches completion in n-docosanol-treated cells, subsequent viral migration to the cell nucleus is significantly inhibited. Thus, the amounts of both HSV core and envelope protein antigens detectable by ELISA, as well as the numbers of infected cells expressing the intranuclear HSV-specific immediate-early protein, ICP-4, by immunofluorescence, are reduced by more than 80%. Finally, the replication of infectious virions as measured in secondary plaque assay cultures is markedly diminished by 99% or more in n-docosanol-treated cells.

To summarize, the presence of n-docosanol has no effect on the initial steps of viral binding, but considerably delays entry of virus into the target cell cytoplasm through some yet-to-be determined mechanism. In addition, the process of migration to, and localization in, the nucleus is substantially blocked, having the ultimate effect of a marked decrease in productive viral replication.

In order to better define the precise mechanism by which n-docosanol exerts its antiviral activity, we have recently studied the cellular uptake, distribution and metabolism of n-docosanol from surfactant-stabilized suspensions. The results of such studies have provided some interesting insight into the metabolic basis of the compound's antiviral action. First, we have been able to show that radioactively-labeled n-docosanol is progressively incorporated into cultured Vero cells, reaching a peak uptake per cell between 6 and 12 hours after exposure. The process is irreversible, since once the compound is cell-associated it cannot be removed even with extensive washing with cesium bromide, which effectively removes nonspecifically-associated cell-bound particles.

Second, at saturating concentrations, less than 1% of the total n-docosanol added to cultures becomes cell-associated within 24 hours. Nonetheless, this corresponds to nearly $8 \times 10^9$ molecules per cell, an astounding amount, which approximates the number of lipid molecules typically found in plasma membranes. The fact that such a small fraction of n-docosanol in the suspension added to cultures becomes cell-associated indicates that the actual bioactive dose is orders of magnitude less than the amount of drug added to the cultures.

Cellular distribution studies examining subcellular fractions recovered by differential centrifugation of sonication disrupted cells demonstrated that after 12 hours of exposure 75% of the radioactive compound is contained in cell membranes, and less than 1% is associated with nuclear fractions; the balance of radioactivity was found associated with the soluble cytoplasmic fraction.

Analyses of the metabolic conversions of n-docosanol have shown that the compound is progressively metabolized to polar compounds, which were demonstrated by thin layer chromatography to be phosphatides, generated either via anabolic (ether linkages) or catabolic (oxidative) reactions. FIG. 10 demonstrates a thin layer chromatographic analysis of a methanol eluted (phosphatide-containing) fraction from a silica gel column of an extract of n-docosanol-treated Vero cells. Nonmetabolized n-docosanol was previously eluted from the silica with chloroform. As shown, approximately 62% of the counts migrated in the region of phosphatidylcholine and 38% migrated in the region of phosphatidylethanolamine. Our studies have also documented that such metabolic conversions can be blocked by appropriate metabolic inhibitors. Thus, the effective energy poisons sodium azide and 2-deoxyglucose reduce both uptake of n-docosanol by Vero cells by 90% and metabolic conversion into polar metabolites by 80%. It is probable that the combination of sodium azide and 2-deoxyglucose mainly inhibits cellular uptake of n-docosanol by inhibiting endocytosis: however other mechanisms of uptake, including an energy-dependent fusion mechanism, or a passive diffusion mechanism facilitated by the subsequent energy-dependent metabolism of n-docosanol, could also be inhibited by these energy poisons.

An interesting aspect of these studies is the indication of a possible role for the polar metabolites of n-docosanol in the antiviral activity of the compound. It has recently been demonstrated that resistance of mouse fibroblasts to polyethylene glycol-induced fusion correlated with an increase in both free fatty alcohols and an elevation in glycerides, including an ether-linked compound that would be analogous to the products obtained via metabolic conversion of n-docosanol as described above. We therefore conducted experiments to investigate the possibility that the enzymatic conversion of n-docosanol is a necessary prerequisite for its antiviral activity. The results of such studies have demonstrated, firstly, that the rate and extent of metabolic conversion, but not that of cellular uptake, of n-docosanol to its polar metabolites is determined by the nature of the surfactant used to suspend the compound and, indeed, that efficiency of metabolic conversion directly correlates with the magnitude of antiviral activity of n-docosanol.

An initial step in conducting such studies involved switching to a different surfactant for suspending n-docosanol. Tetronic 908 is closely related to Pluronic F-68; both are block copolymers of ethylene oxide and propylene oxide. However, whereas Pluronic is a bifunctional polymer with a molecular weight of 8,400, Tetronic 908 is a tetrafunctional copolymer, produced by adding propylene oxide and ethylene oxide to ethylenediamine and resulting in a molecule with an average molecular weight of 25,000. Among other things, when Vero cells are exposed to equivalent doses of n-docosanol suspended in Tetronic versus Pluronic, the rate and extent of metabolism of the compound to polar metabolites is significantly higher with the Tetronic than the Pluronic suspension. The total uptake of radioactive n-docosanol was equivalent from the two different suspension formulations; only the metabolic conversion differed significantly. Correlating with this higher metabolic conversion from Tetronic than Pluronic suspensions is the finding that the $ED_{50}$ for inhibition of HSV replication by n-docosanol is 5–10 mM in Tetronic and approximately 3 times higher in Pluronic. This appears to relate to the 3-fold higher levels of metabolic conversion in cells treated with n-docosanol in Tetronic.

To eliminate the possibility that these findings are peculiar to the Vero cell culture system, we made a reciprocal analysis taking advantage of the fact that, relative to Vero cells, the epithelial-like bovine kidney cell line, MDBK, exhibits an interesting apparent resistance to the anti-HSV activity of n-docosanol. This difference is significant in that n-docosanol is 3–4-fold more effective in inhibiting HSV-induced plaques in Vero cells than in MDBK cells. When we compared total cellular uptake and relative metabolism, the results were strikingly clear. First, both the total amounts of n-docosanol uptake and the relative amounts of metabolic conversion were 3–4 times higher in Vero than in MDBK cells. The combined effect of decreased uptake and decreased metabolism in MDBK versus Vero cells is graphically illustrated in FIG. 11, which shows quite clearly that after 72 hours, Vero cells contain almost 4-fold higher amounts of the phosphatide metabolite, which remains at the origin in this solvent system. Nonetheless, of the counts that are metabolized in two cells lines, the relative amounts in the major classes of phosphatides that are formed, phosphatidylcholine and phosphatidylethanolamine, are not different in the two cell lines. Moreover, pulse-chase experiments showed that both lines eventually convert all of the incorporated counts into the more polar form. Such results suggest that MDBK cells may effectively regulate uptake and/or metabolism of n-docosanol through a feedback type mechanism that is either less effective or nonoperative in Vero cells.

Consistent with the mechanistic observations summarized above, we predicted that n-docosanol would have potential for interfering with a variety of different viruses, specifically those which contain lipid in their outer envelopes and which use fusion mechanisms for entering susceptible target cells. Table 5 summarizes the human and murine lipid-enveloped viruses that, to date, have been shown to be susceptible to the antiviral activity of n-docosanol.

TABLE 6

SPECTRUM OF ANTIVIRAL ACTIVITY OF N-DOCOSANOL* AGAINST LIPID-ENVELOPED VIRUSES

| Human Viruses | Murine Viruses |
|---|---|
| Herpes Simplex - 1 & 2 | Cytomegalovirus |
| Varicella Zoster Virus | Friend Leukemia Virus |
| Human Herpesvirus-6 | LP-BM5 Virus |
| Respiratory Syncytial Virus | |
| Cytomegalovirus | |
| Influenza A | |
| HIV-1 | |

*Or at least one long chain aliphatic alcohol having from 20 to 28 carbon atoms, i.e., n-icosanol, n-henicosanol, n-docosanol, n-tricosanol, n-tetracosanol, n-pentacosanol, n-hexacosanol, n-heptacosanol, and n-octacosanol, or mixtures thereof, n-docosanol alone or mixed with such alcohols being exemplary.

Every lipid-enveloped virus tested can be effectively blocked by this drug. In contrast to its uniform effectiveness against lipid-enveloped viruses, the drug exerted no detectable activity against poliovirus or reovirus, the nonenveloped viruses that we have examined for susceptibility to the compound.

n-Docosanol has anti-retroviral activity both in vitro and in vivo. A formulation possessing anti-retroviral activity and lacking toxicity would have substantial usefulness in treating a variety of retroviral diseases in humans and domestic animals. Notwithstanding the implications for treatment of AIDS, availability of a treatment regimen for diseases caused by retroviruses like feline leukemia virus, bovine leukemia virus, as well HTLV-1 and -2 would have substantial benefits in humanitarian terms. Our studies have established that n-docosanol does inhibit replication of murine retroviruses in vitro and in vivo.

Initial studies focused on the murine Friend leukemia virus (FV; 8). Inoculation of adult mice with FV results in the induction of a leukemia of erythroid progenitors, specifically the basophilic erythroblast. This erythroleukemia is characterized by the rapid proliferation of virus-infected erythroid cells, viremia, immunosuppression, and ultimately death of the animal. Intravenously injected FV will circulate through hematopoietic organs, such as the spleen, and infect erythroid cells. If such infected spleens are fixed on day 10 after virus injection, discrete macroscopic nodules can be seen on the surface of the organ; these represent clones of leukemic cells and form the basis of the spleen focus assay.

The experiment summarized in FIG. 12 illustrates that n-docosanol inhibits Friend Virus-induced leukemia and viremia in adult mice injected intravenously with 75 focus-forming units of Friend Virus. Treated groups were injected intravenously with the varying doses of n-docosanol or Pluronic vehicle alone intravenously on the same day as virus inoculation and once daily for the next 3 days. After 10 days, half of the animals in each group were sacrificed and examined for the presence of leukemic foci in their spleens, while the remaining animals were retained for 10 additional days to monitor viremia. Treatment with n-docosanol exerted a very clear dose-related inhibitory affect on both the development of leukemic foci, shown in Panel A, and the development of viremia, shown in Panel B. In contrast, treatment with comparable amounts of the Pluronic vehicle alone as control exerted no discernible effect. We believe that these results reflect the inhibitory activity of n-docosanol on viral replication, since corollary in vitro studies have documented a very potent activity of this drug against replication of Friend Virus in primary embryo fibroblast cultures.

n-Docosanol inhibits in vitro replication of HIV-1 and human herpes virus 6. Our initial studies on HIV were conducted in collaboration with a U.S. National Institutes of Health laboratory and one of several experiments of this type is summarized in FIG. 13. Normal human peripheral blood mononuclear cells were activated with 1 mg/ml PHA plus 5 units/ml of IL-2 in medium alone or in the presence of the n-docosanol, Pluronic F-68 control vehicle, or phosphonoformic acid (PFA). The next day, the cultures were inoculated with HIV-1 and examined 4 days later for evidence of viral replication by detection of the p24 viral antigen. Substantial levels of HIV-1 replication occurred in the control-treated cultures, comparable to that observed in the untreated group. As shown, n-docosanol exhibited a dose-related inhibitory activity against HIV-1 in cultures of PHA/IL-2-stimulated human peripheral blood mononuclear cells. Activity at the highest dose was comparable to that observed with the very potent antiviral compound, phosphonoformic acid (PFA). Since these initial experiments were conducted, we have reproduced these observations in our own laboratory, showing even higher levels of antiviral HIV activity using the more potent formulation of n-docosanol suspended in Tetronic. The dose response of HIV-1 to n-docosanol indicates an $ED_{50}$ of about 6–9 mM.

To summarize, the initial difficulties experienced in preparing long-term stable cream preparations that contain effective amounts of C-20 to C-28 normal aliphatic alcohols, most preferably consisting essentially of n-docosanol alone or in mixture with other such alcohols, has been overcome and the pharmacology of these compounds has been elucidated. As a composition, the invention is embodied in a long-term stable topical cream formulation that has a shelf-life of greater than a year under normal handling conditions, i.e., is stable for a year or more at room temperatures and will withstand repeated freeze-thaw cycles, suitable for use in treating virus-induced and inflammatory diseases of the skin or membranes of an animal, including the treatment of humans. The essential ingredients of the cream are n-docosanol, alone or in mixture with other normal long chain (C-20 to C-28) aliphatic alcohols, the physiologically active ingredient, water, oil, an ester of a sugar and a fatty acid, the ester being physiologically inert or capable of being metabolized by the body, and an emollient to assist in penetration of the n-docosanol into the affected area of the skin or membrane and coact with the ester in forming a stable carrier for the physiologically active alcohol(s). The sugar-based esters comprise a sugar moiety having a molecular weight of greater than about 150 and preferably above 250 and a fatty acid ester moiety having a molecular weight of about 150 or higher, and preferably above 250. The ester has a molecular weight of about 400 or higher. Sugars, as the term is used here, are sweet or sweetish carbohydrates that are ketonic or aldehydic derivatives of higher polyalcohols, and include both saccharides and disaccharides, disaccharide-based esters being preferred. High molecular weight polyhydric alcohols may be substituted as less desirable equivalents to more traditional sugars.

While it is probably apparent to the reader, the pharmacological studies were conducted using suspensions that are more compatible with the cells used in these studies but which are not suitable as topical pharmaceutical preparations, lacking the body and stability required for effective topical treatment.

A generally optimum cream formulation comprises, by weight based on the total weight of the final cream formulation, n-docosanol, 5–25% or more optimally about 10%±5%, sucrose stearates 0–15%, optimally about 3 to 10%, and/or sucrose cocoate, 0–15%, optimally about 3 to 10%, and/or sucrose distearate 0–15%, optimally about 3 to 10%, at least one sucrose ester or an equivalent sugar-based ester comprising at least about 3 weight percent, preferably about 10±5 weight percent of the total composition, oil, e.g. mineral oil NF 3–15%, optimally about 8%±4%, a glycol, e.g. propylene glycol USP or equivalent, 2–10%, optimally about 5%±2%, an emollient glycol ether, e.g. polyoxypropylene-15-stearyl ether, or benzyl alcohol, 0–5%, optimally about 2–3%, and water 40–70%, optimally about 45 to 65%. Within this general formulation, many specific formulations can be prepared which will be stable and which will exhibit the therapeutic effect noted based upon the data presented above, the teachings of the specification and the guidelines provided in the specification. Herein lies the basis for the first effective topical therapeutic composition wherein the therapeutically active material consists essentially of n-docosanol, alone or in mixture with normal long chain (C-20 to C-28) aliphatic alcohols.

INDUSTRIAL APPLICATION

This invention is useful in the manufacture of pharmaceuticals, and also in the treatment of human and animal patients.

What is claimed is:

1. A therapeutic cream for application to skin and membranes consisting essentially of a sugar-based ester surfactant, greater than about 5% by weight n-docosanol, mineral oil, an emollient co-solvent, and water, for the treatment of viral and inflammatory diseases, wherein said cream is stable at temperatures of at least 40° C. for a period of at least three months and after repeated freeze-thaw cycles.

2. The therapeutic cream of claim 1 wherein the sugar-based ester surfactant is selected from the group consisting of sucrose cocoate, sucrose stearates and sucrose distearate.

3. The therapeutic cream of claim 2 wherein the emollient co-solvent is selected from the group consisting of polyoxypropylene stearyl ether, ethyl hexanediol, and benzyl alcohol, or combinations thereof.

4. A therapeutic cream for application to skin and membranes consisting essentially of a sugar-based ester surfactant, greater than about 5% by weight of at least one long chain aliphatic alcohol having from 20 to 28 carbon atoms selected from the group consisting of n-icosanol, n-henicosanol, n-docosanol, n-tricosanol, n-tetracosanol, n-pentacosanol, n-hexacosanol, n-heptacosanol, and n-octacosanol, or mixtures thereof, mineral oil, an emollient co-solvent, and water, for the treatment of viral and inflammatory diseases, wherein said cream is stable at temperatures of at least 40° C. for a period of at least three months and after repeated freeze-thaw cycles.

5. The therapeutic cream of claim 4 wherein the sugar-based ester surfactant comprises at least one compound selected from the group of sucrose esters consisting of sucrose cocoate, sucrose stearates and sucrose distearate, wherein sucrose ester(s) comprise at least about 3% by weight of the cream.

6. The therapeutic cream of claim 4 wherein sucrose ester(s) comprise at least about 10%±5% by weight of the cream.

7. The therapeutic cream of claim 6 wherein the emollient co-solvent is selected from the group consisting of polyoxypropylene stearyl ether, ethyl hexanediol, and benzyl alcohol, or combinations thereof.

8. The therapeutic cream of claim 7 wherein the long chain aliphatic alcohol comprises at least approximately 10% by weight of the cream.

9. A therapeutic cream comprising a therapeutic composition and a cream base, wherein said therapeutic composition consists essentially of at least one long chain aliphatic alcohol having from 20 to 28 carbon atoms selected from the group consisting of n-icosanol, n-henicosanol, n-docosanol, n-tricosanol, n-tetracosanol, n-pentacosanol, n-hexacosanol, n-heptacosanol, and n-octacosanol, or mixtures thereof, and wherein said cream base comprises one or more compounds selected from the group consisting of sucrose cocoate, sucrose stearates and sucrose distearate and one or more compounds selected from the group consisting of polyoxypropylene stearyl ether, ethyl hexanediol and benzyl alcohol, 10. The therapeutic cream of claim 9 wherein at least one member of the group consisting of sucrose cocoate, sucrose stearates and sucrose distearate is at least about 10%±5% by weight of the cream.

11. The therapeutic cream of claim 10 wherein the long chain aliphatic alcohol having from 20 to 28 carbon atoms comprises at least approximately 10% by weight of the cream.

12. The therapeutic cream of claim 10 wherein the therapeutic composition consists essentially of n-docosanol.

13. The therapeutic cream of claim 10 having the formulation: at least one long chain aliphatic alcohol having from 20 to 28 carbon atoms selected from the group consisting of n-icosanol, n-henicosanol, n-docosanol, n-tricosanol, n-tetracosanol, n-pentacosanol, n-hexacosanol, n-heptacosanol, and n-octacosanol, or mixtures thereof comprising from 5% to 15% by weight of the cream; sucrose stearates comprising from 0% to 15% by weight of the cream; sucrose cocoate comprising from 0% to 10% by weight of the cream; sucrose distearate comprising from 0% to 10% by weight of the cream; with the proviso that at least one sucrose ester be present and comprise at least about 3% by weight of the cream; mineral oil comprising from 3% to 15% by weight of the cream, benzyl alcohol comprising from 0.5% to 10% by weight of the cream; and water comprising from 45% to 70% by weight of the cream.

14. A method of treating viral infections and inflammations of skin and mucous membranes comprising applying a stable therapeutic topical cream to a person in need thereof, said cream comprising a therapeutically active composition consisting essentially of n-docosanol, a cream base consisting essentially of sugar-based ester surfactant, at least one long chain aliphatic alcohol having from 20 to 28 carbon atoms selected from the group consisting of n-icosanol, n-henicosanol, n-docosanol, n-tricosanol, n-tetracosanol, n-pentacosanol, n-hexacosanol, n-heptacosanol, and n-octacosanol, or mixtures thereof, mineral oil, an emollient co-solvent, and water.

15. The method of claim 14 wherein n-docosanol comprises more than one-half of the long chain aliphatic alcohol mixture.

16. A method of treating viral infections and inflammations of skin and mucous membranes comprising applying a topical cream to a person in need thereof having the formulation:

| n-Docosanol | 5-20% by weight |
| Sucrose stearates | 0-15% by weight |
| Sucrose cocoate | 0-10% by weight |
| Sucrose distearate | 0-10% by weight | with the proviso that at least one sucrose ester by present and, wherein sucrose ester(s) comprise about 3% by weight or more of the cream,

| Mineral oil | 3-15% by weight |
| Propylene glycol | 2-10% by weight |
| Polyoxypropylene-15-stearyl ether | 0-5% by weight |
| Benzyl alcohol | 0.5-5% by weight | with the proviso that either polyoxypropylene-15-stearyl ether or benzyl alcohol be present in an amount of at least 1% by weight, and

| Water | 40-70% by weight. |

17. The method of claim 16 wherein sucrose ester(s) comprise about 10%±5% by weight or more of the cream.

18. A cream having the formulation:

| n-Docosanol | 5-20% by weight |
| Sucrose stearates | 0-15% by weight |
| Sucrose cocoate | 0-10% by weight |
| Sucrose distearate | 0-10% by weight | with the proviso that at least one sucrose ester be present and wherein sucrose ester(s) comprise about 3% by weight or more of the cream,

| Mineral oil | 3-15% by weight |
| Propylene glycol | 2-10% by weight |
| Polyoxypropylene stearyl ether | 0-5% by weight |
| Benzyl alcohol | 0-5% by weight | with the proviso that either polyoxypropylene stearyl ether or benzyl alcohol be present in an amount of about 1% by weight or more; and

| Water | 40-70% by weight, | for the prevention or treatment of inflammation or viral infection.

19. The cream of claim 18 wherein sucrose ester(s) comprise about 10%±5% by weight or more of the cream.

20. A method of reducing the pain of a surface inflammation of the skin or membrane comprising applying to an inflamed surface a composition comprising at least one long chain aliphatic alcohol having from 20 to 28 carbon atoms selected from the group consisting of n-icosanol, n-henicosanol, n-docosanol, n-tricosanol, n-tetracosanol, n-pentacosanol, n-hexacosanol, n-heptacosanol, and n-octacosanol, or mixtures thereof, in a physiologically compatible carrier, said alcohol comprising from about 5% to about 25% by weight of said composition.

21. The method of claim 20 wherein the physiologically compatible carrier is a cream base comprising at least one compound selected from the group consisting of sucrose cocoate, sucrose stearates and sucrose distearate and at least one compound selected from the group consisting of polyoxypropylene stearyl ether, ethyl hexanediol and benzyl alcohol.

22. The method of claim 21 wherein the long chain aliphatic alcohol consists essentially of n-docosanol.

* * * * *